(12) United States Patent
Herrmann et al.

(10) Patent No.: US 12,274,765 B2
(45) Date of Patent: *Apr. 15, 2025

(54) CURABLE COMPOSITION FOR PRODUCING A DENTAL COMPOSITE CROWN AND PROCESS OF PRODUCTION

(71) Applicant: Solventum Intellectual Properties Company, Maplewood, MN (US)

(72) Inventors: Andreas Herrmann, Munich (DE); Gioacchino Raia, Türkenfeld (DE); Malte Korten, Moorenweis (DE); Oliver Kappler, Weilheim (DE); Bernhard Hofmann, Peißenberg (DE); Adrian Eckert, Herrsching (DE); Helmar Mayr, Kaufering (DE); Reinhold Hecht, Kaufering (DE); Gallus Schechner, Herrsching (DE); Rainer Guggenberger, Herrsching (DE)

(73) Assignee: Solventum Intellectual Properties Company, Maplewood, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/333,956

(22) Filed: Jun. 13, 2023

(65) Prior Publication Data

US 2023/0320942 A1 Oct. 12, 2023

Related U.S. Application Data

(63) Continuation of application No. 16/622,530, filed as application No. PCT/US2018/036025 on Jun. 5, 2018, now Pat. No. 11,696,875.

(30) Foreign Application Priority Data

Jun. 14, 2017 (EP) .................................... 17176014

(51) Int. Cl.
| | |
|---|---|
| *A61K 6/887* | (2020.01) |
| *A61C 5/73* | (2017.01) |
| *A61K 6/17* | (2020.01) |
| *A61K 6/62* | (2020.01) |
| *A61K 6/65* | (2020.01) |
| *A61K 6/76* | (2020.01) |
| *A61K 6/77* | (2020.01) |
| *C08L 33/08* | (2006.01) |
| *C08L 33/10* | (2006.01) |
| *C08L 75/06* | (2006.01) |

(52) U.S. Cl.
CPC ............... *A61K 6/887* (2020.01); *A61C 5/73* (2017.02); *A61K 6/17* (2020.01); *A61K 6/62* (2020.01); *A61K 6/65* (2020.01); *A61K 6/76* (2020.01); *A61K 6/77* (2020.01); *C08L 33/08* (2013.01); *C08L 33/10* (2013.01); *C08L 75/06* (2013.01)

(58) Field of Classification Search
CPC ..................................................... A61K 6/887
See application file for complete search history.

(56) References Cited

U.S. PATENT DOCUMENTS

| | | | |
|---|---|---|---|
| 4,642,126 | A | 2/1987 | Zador et al. |
| 4,652,274 | A | 3/1987 | Boettcher et al. |
| 4,737,593 | A | 4/1988 | Ellrich et al. |
| 4,795,823 | A | 1/1989 | Schmitt et al. |
| 6,572,693 | B1 | 6/2003 | Wu et al. |
| 6,653,375 | B2 | 11/2003 | Moszner et al. |
| 6,730,156 | B1 | 5/2004 | Windisch et al. |
| 6,899,948 | B2 | 5/2005 | Zhang et al. |
| 6,936,642 | B2 | 8/2005 | Lehmann et al. |
| 7,141,616 | B2 | 11/2006 | Hecht et al. |
| 8,329,776 | B2 | 12/2012 | Hecht et al. |
| 8,651,867 | B2 | 2/2014 | Zilberman |

(Continued)

FOREIGN PATENT DOCUMENTS

| | | |
|---|---|---|
| EP | 2167013 B1 | 12/2010 |
| WO | 2001030304 A1 | 5/2001 |

(Continued)

OTHER PUBLICATIONS

International Search Report for PCT International Application No. PCT/US2018/036025, mailed on Oct. 1, 2018, 5 pages.
Rosentritt, "Regensburg Chewing Simulator. Apparatus for Simulating the Chewing Organ", Material Testing, 1997, vol. 39, No. 03, pp. 77-80.
Esaki, et al., "Basic properties of experimental polymer-based sealant composed of UDMA/dimethacrylate", The Journal of Japanese Society for Dental Materials and Devices, 2011, vol. 30, Issue 1, pp. 63-73.
Musanje, et al., "Effects of Resin Formulation and Nanofiller Surface Treatment on In Vitro Wear of Experimental Hybrid Resin Composite", Journal of Biomedical Materials Research Part B: Applied Biomaterials, 2006, vol. 77B(1), pp. 120-125.

(Continued)

*Primary Examiner* — Michael F Pepitone

(57) ABSTRACT

The invention relates to A curable composition for producing dental composite crowns, the composition comprising a resin matrix comprising polymerizable (meth)acrylate(s) not comprising a urethane moiety, polymerizable urethane (meth)acrylate(s), wherein the polymerizable (meth) acrylate(s) not comprising an urethane moiety are used in excess over the polymerizable urethane(meth)acrylate(s), a filler matrix comprising nanocluster(s), fumed silica in an amount below 8 wt. % with respect to the weight of the whole composition, an initiator system comprising photoinitiator(s), organic dye(s), the curable composition not comprising softener in an amount of more than 5 wt. % with respect to the weight of the whole composition, the curable composition having a viscosity below 150 Pa*s at 23° C. and a shear rate of 1 s$^{-1}$.

The invention also relates to a cured article obtained by radiation curing this curable composition by use of an additive-manufacturing method.

20 Claims, No Drawings

(56) References Cited

U.S. PATENT DOCUMENTS

| | | | |
|---|---|---|---|
| 11,696,875 B2 * | 7/2023 | Herrmann | A61K 6/62 433/228.1 |
| 2004/0161726 A1 | 8/2004 | Saito et al. | |
| 2007/0196792 A1 | 8/2007 | Johnson et al. | |
| 2013/0210959 A1 | 8/2013 | Yang et al. | |
| 2014/0131908 A1 | 5/2014 | Sun et al. | |
| 2015/0111176 A1 | 4/2015 | Wachter et al. | |
| 2016/0136059 A1 | 5/2016 | Hecht et al. | |
| 2016/0184189 A1 | 6/2016 | Hagiwara et al. | |
| 2019/0021815 A1 | 1/2019 | Herrmann et al. | |

FOREIGN PATENT DOCUMENTS

| | | | |
|---|---|---|---|
| WO | 2007098485 A2 | 8/2007 | |
| WO | 2008033758 A2 | 3/2008 | |
| WO | 2009006282 A2 | 1/2009 | |
| WO | 2010045105 A1 | 4/2010 | |
| WO | 2013153183 A2 | 10/2013 | |
| WO | 2015006087 A1 | 1/2015 | |
| WO | 2015126862 A1 | 8/2015 | |
| WO | 2017155692 A1 | 9/2017 | |
| WO | 2019048963 A1 | 3/2019 | |

OTHER PUBLICATIONS

Rodríguez, et al., "Formation of functionalized nanoclusters by solvent evaporation and their effect on the physicochemical properties of dental composite resins", Dental Materials, 2015, vol. 31, pp. 789-798.

* cited by examiner

CURABLE COMPOSITION FOR PRODUCING A DENTAL COMPOSITE CROWN AND PROCESS OF PRODUCTION

CROSS REFERENCE TO RELATED APPLICATIONS

This application is a continuation of U.S. Pat. No. 11,696,875, filed Dec. 13, 2019, which is a national stage filing under 35 U.S.C. 371 of PCT/US2018/036025, filed Jun. 5, 2018, which claims priority to European Pat. Application No. 17176014.3, filed Jun. 14, 2017, the disclosures of each of which are incorporated by reference herein in their entireties.

FIELD OF THE INVENTION

The invention relates to a curable composition suitable for producing dental composite crowns, a prefabricated dental composite crown and a process for producing such a dental composite crown by an additive-manufacturing technique.

BACKGROUND

For treating dental defects a variety of different solutions are meanwhile on the market. Generally, dental defects can be treated by restorative methods or prosthetic methods. Direct restoration composites are for example highly filled materials which are characterized by excellent mechanical properties and low wear. Unfortunately, due to the high filler loading these materials tend to be brittle.

In contrast, temporary crown and bridge materials used as a prosthetic material have a lower filler content. This results in an improved elasticity and a higher fracture resistance, but also in an increased wear which prevents the long-term use of these materials. For an in-office or chairside fabrication of composite indirect restorations there is a need for a material that combines the properties of the materials described above. Prosthetic methods are typically used, if not sufficient remaining tooth structure is left which allows a restorative treatment, e.g. by filling a cavity with a dental filling material. The prosthetic treatment usually starts with taking a dental impression from the dental situation in the mouth of the patient. The obtained record represents the status as is.

In a next step, the tooth to be treated is further prepared, i.e. the tooth is shaped to a form which later allows the fixation of an artificial crown. The artificial crown is typically designed from the information obtained from the dental impression and the shape of the treated tooth. In a next step, the artificial crown is produced in a dental lab and specifically designed for this individual case. This procedure takes time and is expensive.

If, however, a fast and cheap prosthetic treatment is desired, the practitioner might consider using preformed crowns instead. This kind of treatment is often used in pediatric dentistry. Different prefabricated crown types are meanwhile available on the market for this purpose.

A popular solution is the use of stainless steel crowns (e.g. from 3M Oral Care; 3M ESPE). Stainless steel crowns are easy to manufacture and they are also durable over years.

Preformed crowns made from stainless steel have in addition the benefit that they are pre-trimmed, belled and crimped for fast and easy placement. Due to a so-called "snap-on" feature, the stainless steel crown is readily retained and fits over the contour of the prepared tooth.

However, due to its metal surface, stainless steel crowns do not meet the desired aesthetic requirements. To cure this defect, veneered stainless steel crowns have been suggested.

However, veneered stainless steel crowns show only a limited flexibility due to stiffer walls, at least at some areas of the crown. Moreover, chipping of the veneering of these crowns is reported and a metallic shine of the underneath stainless steel crown lowers the esthetic appearance. Thus, it was suggested to try to manufacture preformed crowns out of other materials. Zirconia ceramic ($ZrO_2$) is quite common for individually designed crowns for esthetic dentistry.

$ZrO_2$ has a couple of unique material properties, e.g. high strength and toughness, translucency, stainability and biological compatibility, which makes it well suitable for crowns or even bridges.

However, due to material properties, the side walls of these crowns are not flexible and therefore no undercut design is possible. Further, compared to stainless steel crowns, a different and more invasive tooth preparation without or with a very limited possibility of undercut retention is needed, which leads again to a more careful cementation technique. It has also been suggested to manufacture preformed crowns out of polymeric materials.

In this respect, U.S. Pat. No. 8,651,867 B2 (Zilberman) describes a dental crown configured to be readily mountable in a patient's mouth as part of a treatment of primary teeth and permanent molars, the dental crown having a natural appearance and colour of a vital tooth and consisting of a thermoplastic material layer configured to define a tooth shaped top surface and flexible side surfaces.

As suitable thermoplastic materials polymers selected from polyacetal, polyacrylate, polymethacrylate (PMMA), polyaryletherketone (PAEK), polyetherketon (PEK), polyetheretherketon (PEEK), polyetherimide (PEI), polyethersulfone (PES) and polysulfone (PSU) are suggested.

US 2004/0161726 A1 (Saito et al.) describes a crown prosthesis having wear resistance and an aesthetic property comprising a polymer of a mixture of a polymerizable compound having an unsaturated double bond, a filler and a polymerization initiator, and having an outer shape resembling a tooth and a space to be filled with a dental composite resin between an inner surface thereof and an abutment tooth.

However, the workflow needed for applying polymer material based preformed crowns does not really differ from the workflow needed for applying preformed zirconia crowns, even if a more flexible material is used.

The commercially available polymer based preformed crowns typically show wall thicknesses of more than 500 μm, which gives them not enough flexibility and therefore no undercut design options as an additional support for cementation.

The fact that the material properties do not allow thinner walls makes the walls a limiting factor for the design options.

To nevertheless ensure a sufficient adhesive fixation of these crowns to a prepared tooth surface, an adhesive cementation is recommended or required. This makes the whole prosthetic procedure more complicated and expensive. Generally, for crowns and bridges different cementation techniques are available.

These can be divided into clusters like temporary cementation (e.g. RelyX™ TempNE/E from 3M Oral Care; 3M ESPE), conventional cementation (e.g. Ketac™ CEM or Ketac™ CEM Plus from 3M Oral Care; 3M ESPE), self-adhesive resin cementation (e.g. RelyX™ Unicem from 3M Oral Care; 3M ESPE) or adhesive resin cementation (e.g. RelyX™ Ultimate from 3M Oral Care; 3M ESPE).

In general, the cementation needs to be durable over the life time of the indication, which could be achieved either due to chemical bonding or mechanical retention or a combination thereof.

The choice of the used cement or the general cementation technique for a specific indication is therefore influenced by the material of the restoration, the indication itself, the preparation technique, but also cost and esthetic plays a role.

For a fast and easy chairside workflow with preformed crowns, e.g. pediatric dentistry a fast and easy cementation technique is not only desired but required.

For this reason, for the fixation of stainless steel crowns conventional cementation techniques are used. Those cements do not only have an easier workflow, but also are cheaper than self-adhesive resin or adhesive resin cements. Moreover, they are more moisture tolerant and robust against blood and saliva than self-adhesive or adhesive cements.

This technique is the dominating one in pediatric dentistry, due to the time saving chairside workflow and the fact, that an individually designed crown is not necessarily needed.

WO 2007/098485 A2 (Nusmile) describes a preformed dental crown with a center surface, a circumferential surface transitioning from and integral with the central surface wherein the circumferential surface includes a taper toward a gingival end and wherein said taper has a thickness ranging from 0 to 0.5 mm at a gingival edge to at least 1.0 mm proximate the transition to the center surface.

WO 2008/033758 A2 (3M) describes a solid dental crown including a self-supporting solid hardenable preformed dental crown having an external crown shape defined by an external crown shape defined by an external crown surface.

US 2007/0196792 A1 (Johnson et al.) describes a prefabricated dental crown being tooth coloured and having an undercut. Materials which are said to be useful for manufacturing the prefabricated dental crown are thermoplastic resins such as polyacetal, polyacrylate, polyamide, polyaryletherketone, polyetheretherketone (PEEK), polyetherimide, etc.

WO 2013/153183 (IvoclarVivadent) describes the use of a composite resin composition containing: (a) at least one poly-reactive binder, (b) a first photo-polymerisation initiator with an absorption maximum at a wavelength of less than 400 nm, (c) a second photo-polymerisation initiator with an absorption maximum at a wavelength of at least 400 nm, and (d) an absorber with an absorption maximum at a wavelength of less than 400 nm for the stereo-lithographic production of a dental formed component on the basis of composite resin.

US 2014/131908 (Dentsply) describes a composition for making a three-dimensional dental prosthesis comprising a mixture of 1 to 99.5% of monomer, 5 to 99% of at least one mono or multifunctional (meth)acrylate, 0 to 60% of at least one inorganic filler, 0 to 60% of at least one organic fillers, 5 to 10% a silicone-acrylic-based rubber impact modifier, 0 to 10% pigments, and 0.01 to 10% of light initiators.

U.S. Pat. No. 8,329,776 (Hecht et al.) describes hardenable dental compositions comprises urethane(meth)acrylates, (meth)acrylates, different kind of fillers and initiator.

WO 2015/006087 A1 (3M) describes a hardenable dental composition comprising aggregated nano-sized particles, agglomerated nano-sized particles, (meth)acrylates, urethane(meth)acrylates and a redox curing initiator system.

The hardenable dental compositions described in U.S. Pat. No. 8,329,776 and WO 2015/006087 are typically provided as kit of parts comprising a base paste and a catalyst paste. The hardenable compositions can be used in particular for producing artificial crowns and bridges for temporary or long-term use.

US 2013/0210959 A1 (Yang et al.) describes curable dental compositions comprising a resin system comprising a free-radically polymerizable semi-crystalline resin having a molecular weight no greater than 2000 g/mol and at least 50 wt. % of nano-cluster filler. According to one embodiment, the composition is provided as a preformed dental crown in the form of a hardenable self-supporting structure having a first shape and sufficient malleability to be formed into a second shape. The shaping can be done e.g. by extruding, injection molding, pressing and calendaring.

US 2016/0136059 A1 (Hecht et al.) relates to dental compositions comprising a filler with aggregated non-sized particles and a filler comprising agglomerated nano-sized particles, urethane(meth)acrylates, (meth)acrylates and a redox curing initiator system.

US 2014/0131908 A1 (Sun et al.) relates to a printable polymerizable material system containing a silicone-acrylic-based rubber impact modifier, for making e.g. artificial teeth. The polymerizable material system may contain filler in an amount of 0 to 75 wt. %. In the example section compositions are described containing filler in an amount of more than 55 wt. %.

US 2015/0111176 A1 (Wachter et al.) relates to the use of a composite resin composition comprising a polyreactive binder, a first photopolymerization initiator, a second photopolymerization initiator and an absorber for the stereolithographic production of a dental shaped part based on composite resin. The resin composition also comprises a filler. A filler amount in the range of 50 to 80 wt. % is said to be preferred. As examples compositions are given containing a mixture of Bis-GMA and UDMA in combination with a filler content of more than 60 wt. %. However, none of the solutions suggested in the prior art is completely satisfying.

All these types of crowns do have drawbacks from different aspects, mainly related to a more complex and time-consuming workflow but also due to durability and/or esthetic.

DESCRIPTION OF THE INVENTION

There is a desire for prefabricated composite crowns showing basically the same performance as temporary crowns obtained from commercially available paste/paste materials (e.g. Protemp™ 4; 3M Oral Care), which, however, are in addition autoclavable. Before a particular preformed dental composite crown is finally fixed to the surface of a prepared tooth, it is often required to test various sizes or shapes of different preformed dental composite crowns in the mouth of a patient.

After the testing process, the remaining tested preformed dental composite crowns are contaminated and thus need to be autoclaved before a re-use is possible.

Autoclave conditions typically include the heating of the article in a humid atmosphere for at least 15 min at a temperature of at least 120° C. During such a process, composite articles containing a redox initiator system typically tend to become brittle.

Ideally, the desired prefabricated composite crown should show essentially the same performance before and after an autoclave process has been performed and the respective mechanical values (like E-modulus) should not deviate by e.g. more than about +/−10% with respect to the original value.

Ideally, the prefabricated composite crowns should show a so-called "snap-on effect" comparable to stainless steel crowns.

Further, the prefabricated composite crowns should be easy to manufacture, i.e. it should be possible to efficiently and produce a sufficient volume of crowns.

One or more of the above objects is addressed by the invention described in the present text and the claims.

In one embodiment, the invention features a curable composition for producing dental composite crowns as described in the present text and the claims, the curable composition comprising:
  a resin matrix comprising:
    polymerizable (meth)acrylate(s) not comprising a urethane moiety,
    polymerizable urethane(meth)acrylate(s),
    wherein the polymerizable (meth)acrylate(s) not comprising an urethane moiety are used in excess over the polymerizable urethane(meth)acrylate(s),
  a filler matrix comprising:
    nanocluster(s),
    optionally fumed silica, preferably in an amount below 8 wt. %,
    the filler matrix being present preferably in an amount of 5 to 45 wt. %,
  an initiator system comprising:
    photoinitiator(s),
    organic dye(s),
the curable composition not comprising softener in an amount of more than 5 wt. %, wt. % with respect to the weight of the whole composition,
the curable composition having a viscosity below 150 Pa*s at 23° C. and a shear rate of $1\ s^{-1}$.

The invention also relates to a dental composite crown obtained by curing the curable composition as described in the present text and the claims.

The invention also relates to a process of producing dental composite crowns with an additive manufacturing technique as described in the present text and the claims.

The invention also relates to a kit of parts comprising at least two different dental composite crowns as described in the present text and the claims.

Unless defined differently, for this description the following terms shall have the given meaning:

A "hardenable component or material" or "polymerizable component" is any component which can be cured or solidified by radiation-induced polymerization or crosslinking. A hardenable component may contain only one, two, three or more polymerizable groups. Typical examples of polymerizable groups include unsaturated carbon groups, such as a vinyl group being present i.a. in a (methyl)acrylate group.

A "photoinitiator" is a substance being able to start or initiate the curing process of a polymerizable composition upon exposure to radiation (e.g. wavelength of 350 to 600 nm or 350 to 420 nm).

A "monomer" is any chemical substance which can be characterized by a chemical formula, bearing polymerizable groups (including (meth)acrylate groups) which can be polymerized to oligomers or polymers thereby increasing the molecular weight. The molecular weight of monomers can usually simply be calculated based on the chemical formula given.

As used herein, "(meth)acryl" is a shorthand term referring to "acryl" and/or "methacryl". For example, a "(meth)acryloxy" group is a shorthand term referring to either an acryloxy group (i. e., $CH_2=CH-C(O)-O-$) and/or a methacryloxy group (i. e., $CH_2=C(CH_3)-C(O)-O-$).

A "curing, hardening or setting reaction" is used interchangeable and refers to a reaction, wherein physical properties such as viscosity and hardness of a composition changes over the time due to a chemical reaction between the individual components. A "urethane group" is a group having the structure "—NH—CO—O—".

The term "dental or orthodontic article" means any article which is to be used in the dental or orthodontic field, especially for producing a dental restoration, orthodontic devices, a tooth model and parts thereof.

Examples of dental articles include crowns, bridges, inlays, onlays, veneers, facings, copings, crown and bridged framework, implants, abutments, dental milling blocks, monolithic dental restorations and parts thereof.

Examples of orthodontic articles include brackets, buccal tubes, cleats and buttons and parts thereof.

A dental or orthodontic article should not contain components which are detrimental to the patient's health and thus free of hazardous and toxic components being able to migrate out of the dental or orthodontic article. The surface of a tooth is considered not to be a dental or orthodontic article.

"Glass" means an inorganic non-metallic amorphous material which is thermodynamically an under-cooled and frozen melt. Glass refers to a hard, brittle, transparent solid. Typical examples include soda-lime glass and borosilicate glass. A glass is an inorganic product of fusion which has been cooled to a rigid condition without crystallizing. Most glasses contain silica as their main component and a certain amount of glass former. The material or article described in the present text does typically not contain a glass.

"Glass-ceramic" means an inorganic non-metallic material where one or more crystalline phases are surrounded by a glassy phase so that the material comprises a glass material and a ceramic material in a combination or mixture. Thus, a glass ceramic is a material sharing many properties with both glass and more traditional crystalline ceramics. It is formed as a glass, and then made to crystallize partly by heat treatment. Glass ceramics may refer to a mixture of lithium-, silicon- and aluminium oxides.

A "powder" means a dry, bulk material composed of a large number of fine particles that may flow freely when shaken or tilted.

A "particle" means a substance being a solid having a shape which can be geometrically determined. The shape can be regular or irregular. Particles can typically be analysed with respect to e.g. particle size and particle size distribution. A particle can comprise one or more crystallites. Thus, a particle can comprise one or more crystal phases.

The term "associated" refers to a grouping of two or more primary particles that are aggregated and/or agglomerated. Similarly, the term "non-associated" refers to two or more primary particles that are free or substantially free from aggregation and/or agglomeration.

"Aggregated," as used herein, is descriptive of a strong association of particles often bound together by, for example, residual chemicals treatment or partially sintering. The specific surface of aggregated particles is typically smaller than the specific surface of the primary particles the aggregate is made of (cf. DIN 53206; 1972).

Further breakdown of the aggregates into smaller entities may occur during a polishing step applied to the surface of a composition containing the aggregated filler but not during dispersing the aggregated particles in a resin.

Aggregated fillers and processes for the production and surface treatment thereof are described e.g. in WO 01/30304 and U.S. Pat. No. 6,730,156 (3M). The content of these references is herewith incorporated by reference.

"Agglomerated" is descriptive of a weak association of particles usually held together by charge or polarity and can be broken down into smaller entities.

Agglomerated fillers are commercially available e.g. from Degussa, Cabot Corp or Wacker under the product designation Aerosil™, CAB-O-SIL™ and HDK.

A "non-agglomerated filler" means that the filler particles are present in the resin in a discrete, un-associated (i.e. non-agglomerated and non-aggregated) stage. If desired this can be proven by TEM microscopy.

Non-agglomerated nano-sized silicas are commercially available e.g. from Nalco Chemical Co. (Naperville, Ill.) under the product designation NALCO COLLOIDAL SILICAS e.g. NALCO products #1040, 1042, 1050, 1060, 2327 and 2329.

Non-agglomerated fillers are used and described e.g. in EP 2 167 013 B1 (3M). The content of this reference is herewith incorporated by reference.

The term "primary particle size" refers to the size of a non-associated single crystal zirconia particle, which is considered to be a primary particle. X-ray diffraction (XRD) is typically used to measure the primary particle size.

The mean particle size of a powder can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

A "nano-filler" is a filler, the individual particles thereof have a size in the region of nanometers, e.g. an average particle diameter of less than about 200 nm or less than about 100 nm or less than about 50 nm. Useful examples are given in U.S. Pat. No. 6,899,948/Zhang et al.) and U.S. Pat. No. 6,572,693 (Wu et al.). The content with regard to nano-sized silica particles is herein incorporated by reference.

The measurement of the size of nano-particles is preferably based on a TEM (transmission electron microscopy) method, whereby a population is analyzed to obtain an average particle diameter. A preferred method for measuring the particle diameter can be described as follows:

Samples with a thickness not exceeding 80 nm are placed on 200 mesh copper grids with carbon stabilized formvar substrates (SPI Supplies—a division of Structure Probe, Inc., West Chester, PA). A transmission electron micrograph (TEM) is taken, using JEOL 200CX (JEOL, Ltd. of Akishima, Japan and sold by JEOL USA, Inc.) at 200 KV. A population size of about 50-100 particles can be measured and an average diameter is determined.

"Additive manufacturing" means processes used to make 3-dimensional articles. An example of an additive manufacturing technique is stereolithography (SLA) in which successive layers of material are laid down under computer control and are subsequently cured by radiation. The articles can be of almost any shape or geometry and are produced from a 3-dimensional model or other electronic data source. Other examples of additive manufacturing processes or techniques include 3d-printing.

"Resin modified glass ionomer cement" means a hardenable dental material comprising acid-reactive glass, polyacid, water, polymerizable components and initiator. Resin modified glass ionomer cements undergo a twofold curing reaction, a glass ionomer acid base based cement reaction and polymerization of typically (methacrylate) acrylate based monomers.

"Adhesive resin cement" means a hardenable dental material which cures by radical polymerization of polymerizable components (but not by a glass ionomer cement reaction). An adhesive resin cement requires a pre-treatment of the hard dental surfaces to effect adhesion. In contrast to resin modified glass ionomer cements, an adhesive resin cement does not contain added water.

A "self-adhesive resin cement" is an adhesive resin cement which in addition contains acidic components and thus does not require a pre-treatment of the hard dental surfaces to effect adhesion.

In contrast to resin modified glass ionomer cements, adhesive resin cement and self-adhesive resin cement typically only cure by polymerization reaction.

"Density" means the ratio of mass to volume of an object. The unit of density is typically $g/cm^3$. The density of an object can be calculated e.g. by determining its volume (e.g. by calculation or applying the Archimedes principle or method) and measuring its mass.

The volume of a sample can be determined based on the overall outer dimensions of the sample. The density of the sample can be calculated from the measured sample volume and the sample mass. The total volume of a material sample can be calculated from the mass of the sample and the density of the used material. The total volume of cells in the sample is assumed to be the remainder of the sample volume (100% minus the total volume of material).

A material or composition is "essentially or substantially free of" a certain component within the meaning of the invention, if the material or composition does not contain said component as an essential feature. Thus, said component is not wilfully added to the composition or material either as such or in combination with other components or ingredient of other components. A composition or material being essentially free of a certain component usually contains the component in an amount of less than 1 wt. % or less than 0.1 wt. % or less than 0.01 wt. % (or less than 0.05 mol/l solvent or less than 0.005 mol/l solvent or less than 0.0005 mol/l solvent) with respect to the whole composition or material. Ideally the composition or material does not contain the said component at all. However, sometimes the presence of a small amount of the said component is not avoidable e.g. due to impurities.

"Ambient conditions" mean the conditions which the inventive composition is usually subjected to during storage and handling. Ambient conditions may, for example, be a pressure of 900 to 1100 mbar, a temperature of −10 to 60° C. and a relative humidity of 10 to 100%. In the laboratory ambient conditions are adjusted to about 23° C. and about 1013 mbar. In the dental and orthodontic field ambient conditions are reasonably understood as a pressure of 950 to 1050 mbar, temperature of 15 to 40° C. and relative humidity of 20 to 80%.

As used herein, "a", "an", "the", "at least one" and "one or more" are used interchangeably. The terms "comprise" or "contain" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive (s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about". The term "comprise" shall include also the terms "consist essentially of" and "consists of".

DETAILED DESCRIPTION

The invention described in the present text is advantageous for a couple of reasons. The curable composition described in the present text can be easily processed as construction material in an additive manufacturing process comprising a radiation step, in particular using a stereolithographie technique (SLA technique).

Without wishing to be bound to a certain theory, it is believed that the viscosity of the curable composition contributes to an easy processing of the composition in an additive-manufacturing technique.

This allows also the simultaneous production of more individualized composite crowns.

Further, without wishing to be bound to a certain theory, it is believed that due to the limited amount or even absence of softeners, the cured composition becomes better autoclavable.

Softeners are typically present in curable composition for use as temporary crown and bridge materials which are provided as kit of parts comprising a base paste and a catalyst paste. These softeners may migrate out of the cured composite article during an autoclave process.

As the curable composition described in the present text does typically not contain softener or only in small amounts, the risk that softeners migrate out from the cured composition during an autoclave process is reduced.

Nevertheless, it was found that the mechanical properties of the cured composition remain fairly unchanged after an autoclaving has been conducted.

Further, the obtained printed article often shows less defects and inhomogeneity compared to articles obtained by curing a redox-initiator containing curable composition, which has been provided by mixing a catalyst and base paste either by hand or by using a static mixing tip.

The curable composition described in the present text enables the production of 3-dim articles or products with precise build features and smooth surfaces.

It was also found that the curable composition described in the present text allows the production of 3-dimensional structures with wall thicknesses below 0.8 mm.

Further, the curable composition described in the present text allows the production of prefabricated composite crowns having the desired "snap-on effect" comparable to stainless steel crowns.

Thus, the article obtained after having processed the curable composition as construction material in an additive manufacturing process is characterized by a combination of specific properties such as high mechanical strength, high fracture resistance and high aesthetics.

The curable composition is in particular useful in the dental and orthodontic field and may also facilitates the chair-side production of indirect dental restorations on the same day.

Examples of such indirect dental restorations include dental crowns and bridges, in particular preformed dental composite crowns having a shape which has an undercut structure.

Such a shape provides the crown with a so-called "snap-on effect" and allows an easy placement of the preformed composite crown on the surface of a prepared tooth, in particular in the pediatric field.

In certain embodiments, the curable composition fulfils one or more, sometimes all of the following properties:
a) curable by radiation having a wavelength of in the range of 350 to 600 nm or 350 to 420 nm;
b) viscosity: 1 to 100 Pa*s at 23° C. at a shear rate of 1 $s^{-1}$;
c) pH value: 6 to 8, if brought in contact with wet pH sensitive paper.

If desired, the properties can be measured as described in the example section.

In certain embodiments, the combination of the following features is sometimes desirable: a) and b), or a), b) and c).

The curable composition described in the present text is radiation curable in a wave length which is typically used in commercially available additive manufacturing equipment.

Further, the curable composition described in the present text typically has a viscosity which allows the processing of the composition in an SLA process. A lower viscosity often allows a better printing quality in particular as regards surface accuracy.

The curable composition described in the present text is typically opaque.

As the curable composition does typically not contain acidic components, the pH value of the composition is in the neutral range.

The curable composition described in the present text comprises a resin matrix.

The resin matrix typically comprises 40 to 90 wt. % or 50 to 80 wt. % of the curable composition.

The resin matrix comprises polymerizable (meth) acrylate(s) not comprising a urethane moiety as component (A) and polymerizable urethane(meth)acrylate(s) as component (B).

The resin of the curable composition also comprises a (meth)acrylate(s) having at least 1 or 2 polymerizable moieties but not comprising a urethane moiety.

Thus, the (meth)acrylate(s) is different from urethane (meth)acrylate, e.g. with respect to functionality, chemical moieties, molecular weight or combinations thereof.

If desired, the chemical composition may comprise at least two, three or four different kinds of (meth)acrylate(s).

Adding a (meth)acrylate to the resin composition helps to further improve the mechanical properties of the resin composition in its cured stage, in particular with regards to flexural strength or abrasion resistance.

The molecular weight of the (meth)acrylate(s) is typically at least 170 or at least 200 or at least 300 g/mol.

The molecular weight of the (meth)acrylate(s) is typically in a range of 170 to 3,000 or 200 to 2,500 or 300 to 2,000 g/mol.

The (meth)acrylate(s) has free radically active functional groups and includes monomers, oligomers, and polymers having two or more ethylenically unsaturated groups.

Such free radically polymerizable materials include di- or poly-acrylates and methacrylates such glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethyl-methane; the bis-acrylates and bis-methacrylates of polyethylene glycols of molecular weight 200-500, copolymerizable mixtures of acrylated monomers such as those in U.S. Pat. No. 4,652,274, and acrylated oligomers such as those of U.S. Pat. No. 4,642,126; and vinyl compounds such as diallyl phthalate, divinyl succinate, divinyl adipate and divinylphthalate.

Preferred ethylenically unsaturated monomers are methacrylate and acrylate monomers, such as di(meth)acrylates of propanediol, butanediol, hexanediol, octanediol, nonanediol, decanediol and eicosanediol, di(meth)acrylates of ethylene glycol, of polyethylene glycols and of polypropylene glycols, di(meth)acrylates of ethoxylated bisphenol A, for example 2,2'-bis(4-(meth)acryloxytetraethoxyphenyl)propanes, and (meth)acrylamides. The monomers used can furthermore be esters of [alpha]-cyanoacrylic acid, crotonic acid, cinnamic acid and sorbic acid.

It is also possible to use the methacrylic esters mentioned in EP 0 235 826 A1 (ESPE), such as bis[3 [4]-methacryl-oxymethyl-8(9)-tricyclo[5.2.1.0$^{2,6}$]decylmethyl triglycolate. Particularly suitable are 2,2-bis-4(3-methacryloxy-2-hydroxypropoxy)phenylpropane (Bis-GMA), 2,2-bis-4(3-methacryloxypropoxy)-phenylpropane, triethylene glycol dimethacrylate (TEGDMA), and di(meth)acrylates of bis-hydroxymethyltricyclo-(5.2.1.0$^{2,6}$)decane.

It was found that using (meth)acrylate(s) and more particularly, the components described above, can be beneficial to provide the hardened composition with sufficient mechanical strength as it may function as a kind of cross-linking agent useful for improving the mechanical properties of the cured dental composition.

The (meth)acrylate(s) is typically present in the following amounts:
  lower amount: at least 40 or at least 45 or at least 50 wt. %;
  upper amount: utmost 85 or utmost 80 or utmost 70 wt. %;
  range: 40 to 85 or 45 to 80 or 50 to 70 wt. %;
wt. % with respect to the weight of the polymerizable composition.

The polymerizable (meth)acrylates not containing a urethane moiety are used in excess compared to the polymerizable urethane(meth)acrylates.

The following ratio was found to be suitable:
[polymerizable (meth)acrylates not containing a urethane moiety]/[polymerizable urethane (meth)acrylates] from 5:1 to 1.5:1.

The curable composition comprises at least one, two, three or four different kinds of urethane(meth)acrylate(s).

It was found that the addition of urethane(meth)acrylate(s) to the resin matrix contributes to improving certain mechanical properties like E-modulus and fracture work of the cured composition. The molecular weight of the urethane(meth)acrylate is typically at least 450 or at least 800 or at least 1,000 g/mol. Useful ranges include 450 to 3,000 or 800 to 2,700 or 1,000 to 2,500 g/mol.

Molecules having a molecular weight above 450 g/mol or above 1,000 g/mol are usually less volatile than molecules having a lower molecular weight and thus may contribute to providing a biocompatible composition.

Further, a sufficiently high molecular weight of the urethane(meth)acrylate may contribute to the desired fracture work of the composition after hardening.

The nature and structure of the urethane(meth)acrylate is not particularly limited unless the desired result cannot be achieved.

Urethane (meth)acrylates may be obtained by a number of processes known to the skilled person.

The urethane(meth)acrylates employed in the composition are typically obtained by reacting an NCO-terminated compound with a suitable monofunctional (meth)acrylate monomer such as hydroxyethyl acrylate, hydroxyethyl methacrylate, hydroxypropylmethacrylate, preferably hydroxyethyl- and hydroxypropylmethacrylate.

For example, a polyisocyanate and a polyol may be reacted to form an isocyanate-terminated urethane prepolymer that is subsequently reacted with a (meth)acrylate such as 2-hydroxy ethyl(meth)acrylate. These types of reactions may be conducted at room temperature or higher temperature, optionally in the presence of catalysts such as tin catalysts, tertiary amines and the like.

Polyisocyanates which can be employed to form isocyanate-functional urethane prepolymers can be any organic isocyanate having at least two free isocyanate groups. Included are aliphatic cycloaliphatic, aromatic and araliphatic isocyanates.

Any of the known polyisocyanates such as alkyl and alkylene polyisocyanates, cycloalkyl and cycloalkylene polyisocyanates, and combinations such as alkylene and cycloalkylene polyisocyanates can be employed.

Preferably, diisocyanates having the formula $X(NCO)_2$ are used, with X representing an aliphatic hydrocarbon radical with 2 to 12 C atoms, a cycloaliphatic hydrocarbon radical with 5 to 18 C atoms, an aromatic hydrocarbon radical with 6 to 16 C atoms and/or an araliphatic hydrocarbon radical with 7 to 15 C atoms.

Examples of suitable polyisocyanates include 2,2,4-trimethylhexamethylene-1,6-diisocyanate, hexamethylene-1,6-diisocyanate (HDI), cyclohexyl-1,4-diisocyanate, 4,4'methylene-bis(cyclohexyl isocyanate), 1,1'-methylenebis(4-isocyanato) cyclohexane, isophorone diisocyanate, 4,4'-methylene diphenyl diisocyanate, 1,4-tetramethylene diisocycanate, meta- and para-tetramethylxylene diisocycanate, 1,4-phenylene diisocycanate, 2,6- and 2,4-toluene diisocycanate, 1,5-naphthylene diisocycanate, 2,4' and 4,4'-diphenylmethane diisocycanate and mixtures thereof.

It is also possible to use higher-functional polyisocyanates known from polyurethane chemistry or else modified polyisocyanates, for example containing carbodiimide groups, allophanate groups, isocyanurate groups and/or biuret groups. Particularly preferred isocyanates are isophorone diisocyanate, 2,4,4-trimethyl-hexamethylene diisocyanate and higher-functional polyisocyanates with isocyanurate structure.

The isocyanate terminated urethane compound is capped with a (meth)acrylate to produce a urethane(meth)acrylate compound. In general, any (meth)acrylate-type capping agent having a terminal hydroxyl group and also having an acrylic or methacrylic moiety can be employed, with the methacrylic moiety being preferred.

Examples of suitable capping agents include 2-hydroxyethyl(meth)acrylate, 2-hydroxypropyl (meth)acrylate, glycerol di(meth)acrylate and/or trimethylolpropane di(meth)acrylate. Particularly preferred are 2-hydroxyethyl methacrylate (HEMA) and/or 2-hydroxyethyl acrylate (HEA).

The equivalence ratio of isocyanate groups to compounds reactive vis-à-vis isocyanate groups is 1.1:1 to 8:1, preferably 1.5:1 to 4:1.

The isocyanate polyaddition reaction can take place in the presence of catalysts known from polyurethane chemistry, for example organotin compounds such as dibutyltin dilaurate or amine catalysts such as diazabicyclo[2.2.2]octane. Furthermore, the synthesis can take place both in the melt or in a suitable solvent which can be added before or during the prepolymer preparation. Suitable solvents are for example acetone, 2-butanone, tetrahydrofurane, dioxane, dimethylformamide, N-methyl-2-pyrrolidone (NMP), ethyl acetate, alkyl ethers of ethylene and propylene glycol and aromatic hydrocarbons. The use of ethyl acetate as solvent is particularly preferred.

Suitable examples of urethane (meth)acrylates include 7,7,9-trimethyl-4,13-dioxo-3,14-dioxa-5,12-diazahexadecane-1,16-dioxy-dimethacrylate (e.g. Plex 666-1, Rohm), 7,7,9-trimethyl-4,13-dioxo-5,12-diazahexadecane-1,16-dioxy-dimethacrylate (UDMA), urethane (methacrylates) derived from 1,4 and 1,3-Bis(1-isocyanato-1-methylethyl) bezene (e.g. as described in EP 0934926 A1) and mixtures thereof.

According to one embodiment, the urethane(meth)acrylate is characterized as follows:
having the structure A-(-S1-U-S2-MA)$_n$, with
A being a connector element comprising at least one unit,
S1 being a spacergroup comprising at least 4 units connected with each other,
S2 being a spacergroup comprising at least 4 units connected with each other,
the units of A, S1 and S2 being independently selected from CH$_3$—, —CH$_2$—, —O—, —S—, —NR$^1$—, —CO—, —CR$^1$=,

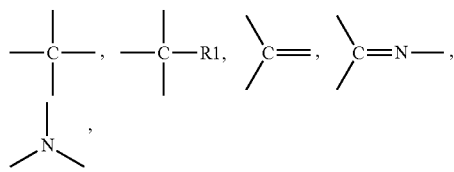

—N=, —CR$^1$R$^2$—,
with R$^1$ and R$^2$ being independently selected from hydrogen, alkyl, substituted alkyl, alkenyl, cycloalkyl, substituted cycloalkyl, arylalkyl, aryl or substituted aryl, wherein these units can form linear, branched or cyclic structures such as alkyl, cycloalkyl, aryl, ester, urethane or amide groups,
U being a urethane group connecting spacergroups S1 and S2,
MA being an acrylate or methacrylate group and
n being 3 to 6.

According to one embodiment the urethane(meth)acrylate is represented by the structure A-(-S1-U-S2-MA)$_n$ with
A being a connector element comprising at least about 1, 2, 3, 4, 5, 6, 7, 8, 9, 10, 11, 12, 13, 14, 15, 16, 17, 18, 19 or 20 units,
S1 being a spacergroup comprised of units connected with each other and comprising at least about 4, 5, 6, 7, 8, 9 or 10 units,
S2 being a spacergroup comprised of units connected with each other and comprising at least about 4, 5, 6, 7, 8, 9, 10, 12, 15, 20 or 25 units,
U being a urethane group connecting spacergroups S1 and S2,
MA being an acrylate or methacrylate group and
n being 3 to 6 or 4 to 6 or 5 to 6.

It can be preferred, if A has a cyclic structure and comprises at least about 6 units.

It can further be preferred, if S1 has a linear or branched structure and comprises at least about 4 or about 6 units.

It can further be preferred, if S2 has a linear or branched structure and comprises at least about 6 or about 8 units.

A urethane(meth)acrylate wherein A has a cyclic structure and comprises at least about 6 units and S1 has a linear structure and comprises at least about 4 units and S2 has a linear structure and comprises at least about 8 units and U is a urethane group can also be preferred.

Neither the atoms of the urethane group connecting S1 and S2 nor the atoms of the (meth)acrylgroup belong to the spacergroup S1 or S2. Thus, the atoms of the urethane group do not count as units of the spacergroups S1 or S2.

The nature and structure of the connector element is not particularly limited. The connector element can contain saturated (no double bonds) or unsaturated (at least one or two double bonds) units, aromatic or hetero aromatic units (aromatic structure containing atoms including N, O and S).

Specific examples of connector element A having a cyclic structure include:

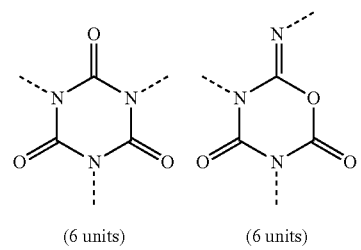

(6 units)  (6 units)

Specific examples of connector element A having a non-cyclic but branched structure include:

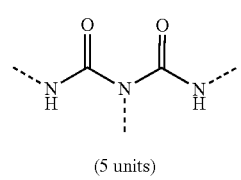

(5 units)

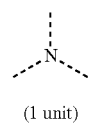

(1 unit)

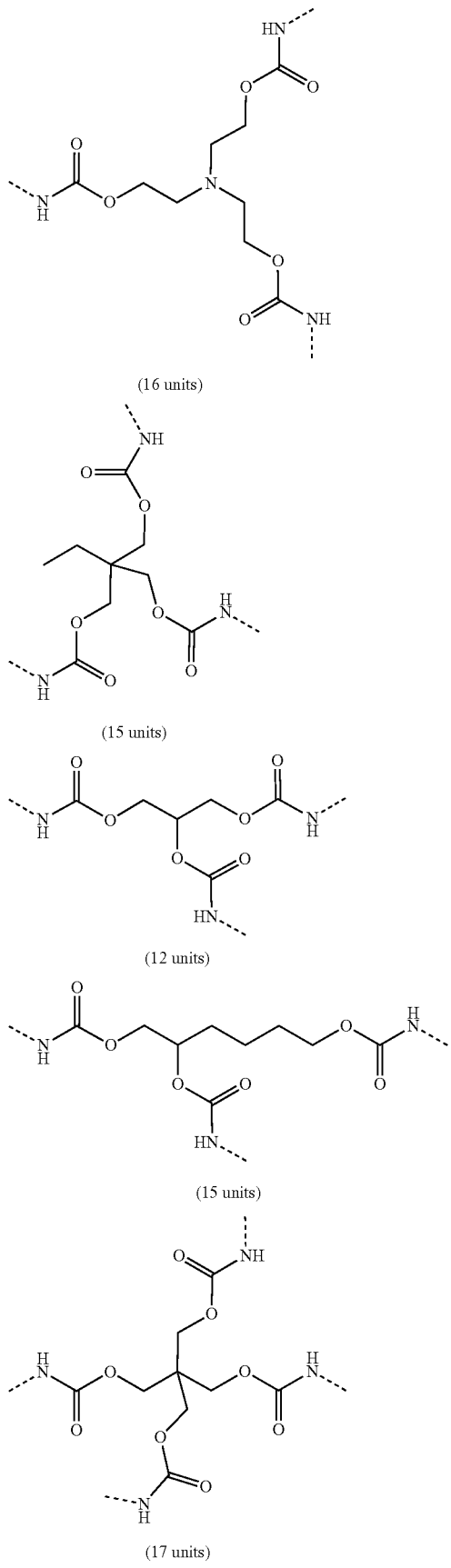

(16 units)

(15 units)

(12 units)

(15 units)

(17 units)

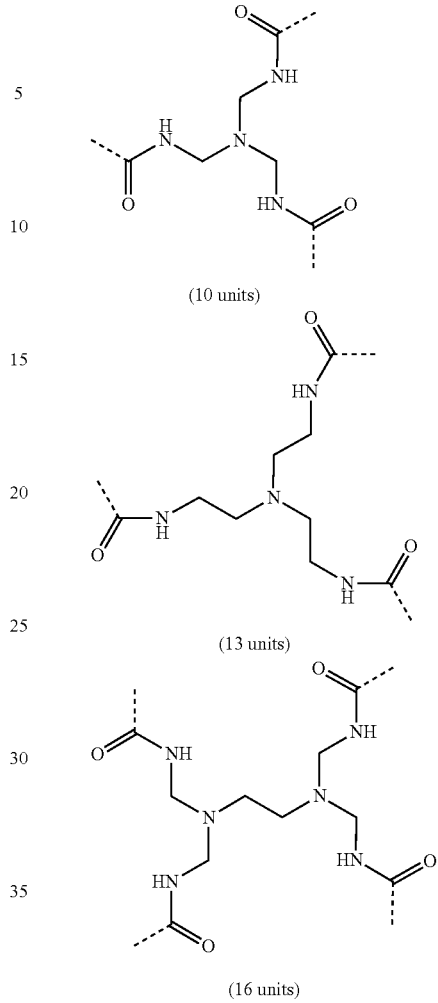

(10 units)

(13 units)

(16 units)

The dotted lines indicate the bondings to the spacergroup S1.

the nature and structure of the spacergroups S1 or S2 is not particularly limited, either.

The spacergroups are comprised of units connected with each other. Typical units include: $CH_3-$, $-CH_2-$, $-O-$, $-S-$, $-NR^1-$, $-CO-$, $-CR^1=$,

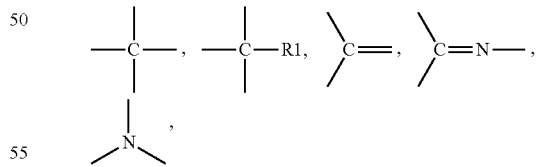

$N=$, $-CR^1R^2-$, with $R^1$ and $R^2$ independently selected from hydrogen, alkyl, substituted alkyl, alkenyl, cycloalkyl, substituted cycloalkyl, arylalkyl, aryl or substituted aryl.

These units can form linear, branched or cyclic structures such as alkyl, cycloalkyl, aryl, ester, urethane or amide groups.

The structure of S1 can be identical to the structure of S2. However, in some embodiments the structure of S1 is different from S2. In a specific embodiment the number of units being present in S1 is less or equal than the number of units being present in S2.

In a specific embodiment, S1 may have a saturated hydrocarbon structure.

In another specific embodiment, S2 may have a saturated hydrocarbon structure.

Typical examples of useful spacer groups for S1 include:

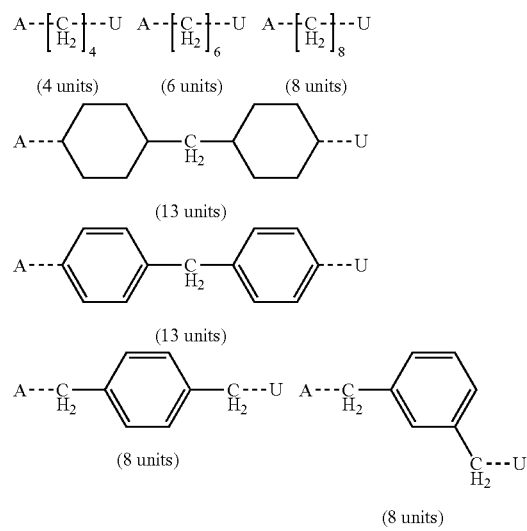

the dotted lines indicate the chemical bonding to either the group A or the group U.

Typical examples of useful spacer groups for S2 include:

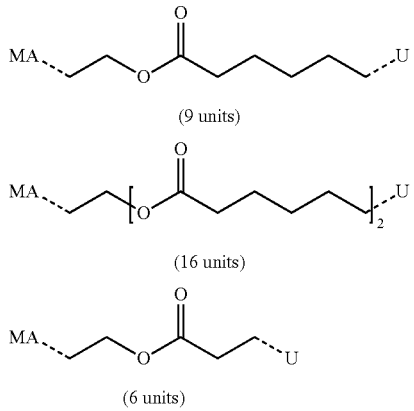

The dotted lines indicate the chemical bonding to either the (meth)acrylate group or the group U. The number of the units to be counted according to the invention is given in brackets.

Specific examples of hardenable component (B) include:

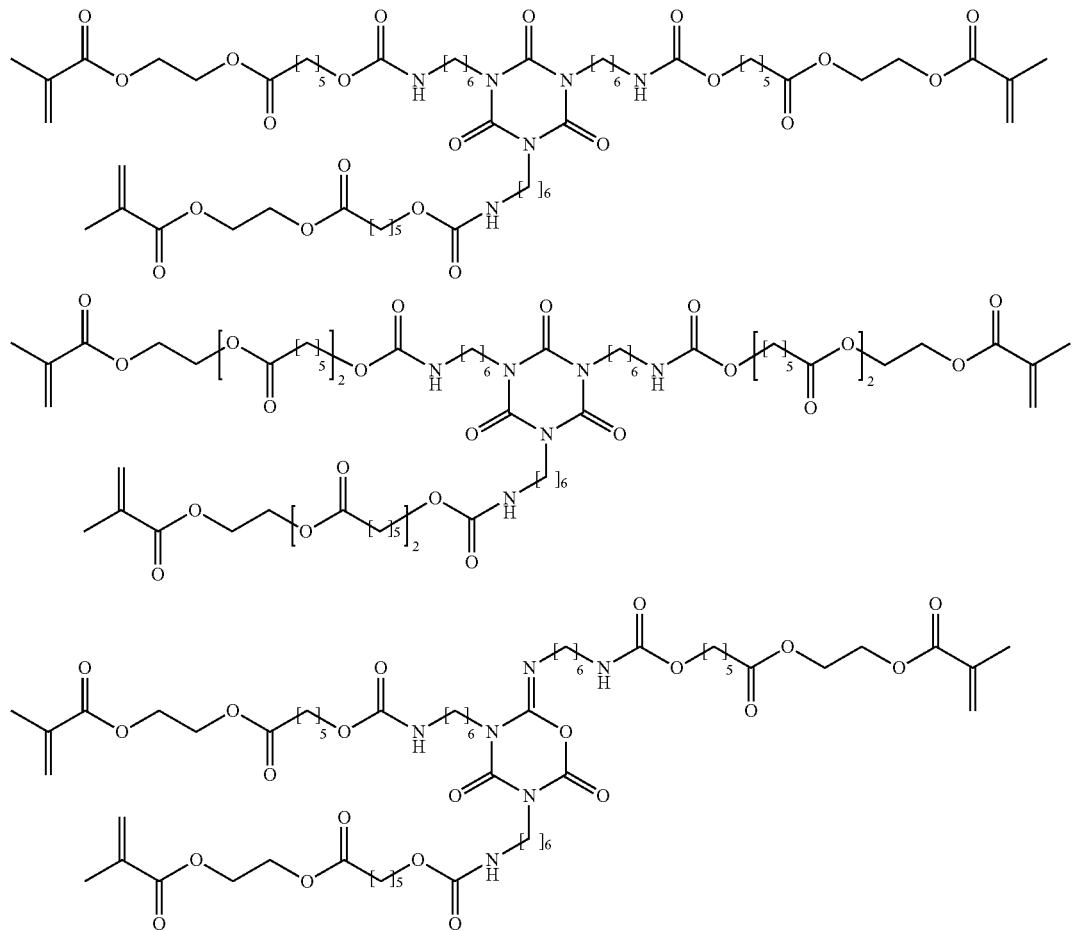

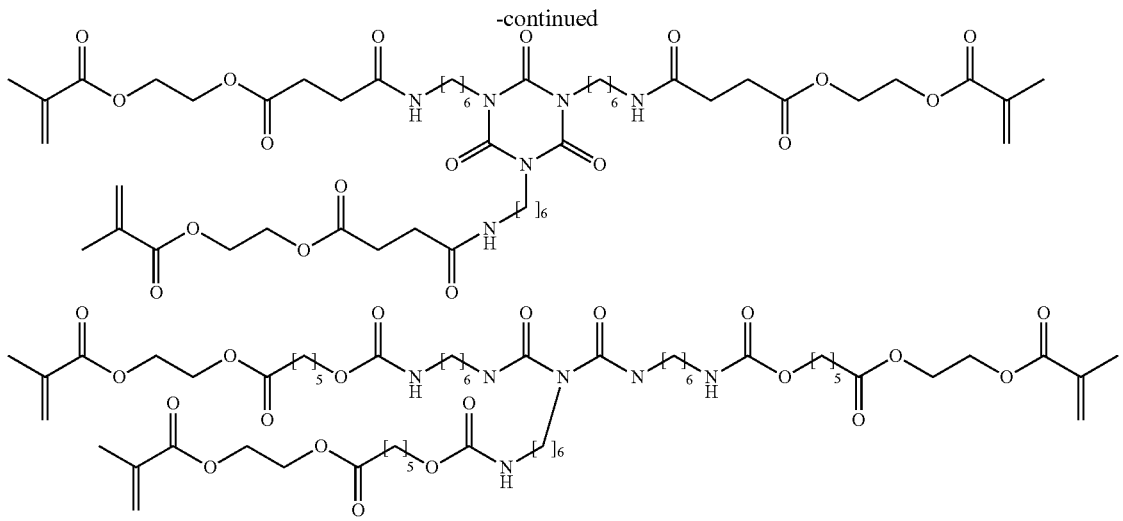

Further suitable urethane(meth)acrylates are based on α,ω-terminated poly(meth)acrylatdiols (e.g. as described in EP 1 242 493 B1) or can be a polyester, polyether, polybutadiene or polycarbonate urethane(meth)acrylate (e.g. as described in U.S. Pat. No. 6,936,642 B2).

The urethane(meth)acrylate is typically present in the following amounts:
Lower amount: at least 1 or at least 3 or at least 5 wt. %;
Upper amount: utmost 35 or utmost 30 or utmost 25 wt. %;
Range: 1 to 35 or 3 to 30 or 5 to 25 wt. %;
wt. % with respect to the weight of the polymerizable composition.

If the amount of urethane(meth)acrylate is too high, the resulting material might become too flexible and will probably not maintain its desired shape.

If the amount of urethane(meth)acrylate is too low, the resulting material might become too brittle. Fracture work and impact strength might be negatively affected.

The curable composition described in the present text comprises a filler matrix.

The filler matrix is typically present in an amount from 5 to 45 wt. % or from 10 to 40 wt. %.

The amount of filler used may have an impact on the viscosity of the curable composition, the abrasion resistance of the cured composition or both.

The filler matrix may comprise fumed silica.

The specific surface of the hydrophobic fumed silica is typically from 100 to 300 or from 150 to 250 m²/g.

A mixture of different fumed silica can be used, if desired. E.g. a mixture of fumed silica the surface of which has been treated with a hydrophobic surface treating agent and fumed silica the surface of which has been treated with a hydrophilic surface treating agent can be used.

Suitable hydrophobic surface-treating agents include:
—OSiR₃, with R being selected from $C_{1-4}$ alkyl, preferably methyl and mixtures thereof.

Hydrophobic fumed silica is also commercially available under the trade designations HDK, in particular HDK-H™ 2000 (Wacker), or Aerosil™ R812 (Evonik).

It was found that using fumed silica the surface of which has been treated with surface treating agents containing polymerizable moieties, like (meth)acrylsilanes, may sometimes lead to a non-desired thickening of the curable composition, which may make the curable composition less suitable as processing material in an additive manufacturing process.

Thus, according to one embodiment the curable composition described in the present text does typically not contain fumed silica having been surface treated with surface treating agents containing polymerizable moieties like (meth)acrylsilanes, in an amount of more than 2 wt. % or more than 1.5 wt. % or more than 1 wt. %.

If present, fumed silica is typically present in either of the following amounts:
Lower amount: at least 0.5 or at least 1 or at least 1.5 wt. %;
Higher amount: utmost 8 or utmost 7 or utmost 5 wt. %;
Range: 0.5 to 8 or 1 to 7 or 1.5 to 5 wt. %;
wt. % with respect to the weight of the whole curable composition.

The filler matrix comprises nanocluster(s). One or more different kinds of nanocluster(s) can be present.

It was found that compared to other fillers, using nanocluster(s) can be beneficial because it allows for the formulation of a composition with high filler load resulting in better mechanical properties, e.g. polishability or abrasion and in higher aesthetics.

The nanocluster can typically be characterized by at least one or all of the following features:
Specific surface: 30 to 400 or 60 to 300 or 80 to 250 m²/g, comprising particles of $SiO_2$, $ZrO_2$, $Al_2O_3$ and mixtures thereof.

If desired, the specific surface can be determined according to Brunauer, Emmet and Teller (BET) by using a device (Monosorb™) available from Quantachrome.

If desired, the mean particle size can be determined by light scattering using e.g. a Malvern Mastersizer 2000 device available from Malvern Instruments.

A suitable nano-filler comprising aggregated nano-sized particles can be produced according to the processes described e.g. in U.S. Pat. No. 6,730,156 (preparatory example A).

A useful nano-filler comprising aggregated nano-sized particles can be prepared from a suitable sol and one or more oxygen containing heavy metal compound solution(s) precursors which may be salts, sols, solutions, or nano-sized particles; of these, sols are preferred. For purposes of this invention, a sol is defined as a stable dispersion of colloidal solid particles within a liquid. The solid particles are typically denser than the surrounding liquid and small enough so that the dispersion forces are greater than the gravitational force. In addition, the particles are of a size small enough so that they generally do not refract visible light. Judicious choice of the precursor sols leads to desired degree of visual opacity, strength etc. Factors that will guide the choice of the sol depends on the combination of the following properties: a) the average size of the individual particles, which is preferably less than 100 nm in diameter, b) the acidity: the pH of the sol should be preferably below 6 and more preferably below 4, and c) the sol should be free of impurities that cause undue aggregation (during the filler preparation process) of the individual discrete particles, during the subsequent steps such as spray drying or calcining, into larger size particles that cannot be easily dispersed or commuted and hence decrease the translucency and polishability of a dental restoration made out of a composite comprising such nanoparticles.

If the starting sol is basic, it should be acidified e.g. by addition of nitric or other suitable acid to decrease the pH. However, choosing a basic starting sol is less desirable since it requires an additional step and may lead to the introduction of undesired impurities. Typical impurities that are preferably avoided are metal salts, particularly salts of alkaline metals e.g. sodium.

The non-heavy metal sol and heavy metal oxide precursors are mixed together preferably at a molar ratio to match the index of refraction of the hardenable resin. This imparts a low and desirable visual opacity. Preferably, the molar ratio ranges of non-heavy metal oxide ("non-HMO") to heavy metal oxide ("HMO"), expressed as non-HMO:HMO is 0.5:1 to 10:1, more preferably 3:1 to 9:1, and most preferable 4:1 to 7:1.

In a preferred embodiment where the aggregated nano-sized particles contain silica and zirconium containing compounds, the method of preparation starts with a mixture of silica sol and zirconyl acetate, at about a 5.5:1 molar ratio.

Prior to mixing the non-heavy metal oxide sol with the heavy metal oxide precursor, the pH of the non-heavy metal oxide sol is preferably reduced to provide an acidic solution having a pH of 1.5 to 4.0.

The non-heavy metal oxide sol is then slowly mixed with the solution containing the heavy metal oxide precursor and vigorously agitated. Strong agitation is preferably performed throughout the blending process. The solution is then dried to remove the water and other volatile components. Drying can be accomplished in various ways, including for example, tray drying, fluidized bed and spray drying. In the preferred method where zirconyl acetate is used, drying by means of spray drying.

The resulting dried material is preferably made up of small substantially spherical particles as well as broken hollow spheres. These fragments are then batch calcined to further remove residual organics. The removal of the residual organics allows the filler to become more brittle, which results in more efficient particle size reduction. During calcining, the soak temperature is preferably set at 200° C. to 800° C., more preferably 300° C. to 600° C. Soaking is performed for 0.5 hours to 8 hours, depending on the amount of material being calcined. It is preferred that the soak time of the calcine step be such that a plateaued surface area is obtained. It is preferred that the time and temperature be chosen such that the resulting filler is white in colour, free from black, grey, or amber coloured particles, as determined by visual inspection.

The calcined material is then preferably milled to a median particle size of less than 5 μm, preferably less than 2 μm (on a volumetric basis), as can be determined by using a Sedigraph 5100 (Micrometrics, Norcross, Ga.). The particle size determination can be performed by first obtaining the specific density of the filler using an Accuracy 1330 Pycometer (Micrometrics, Norcross, Ga.). Milling can be accomplished by various methods including for example, stirred milling, vibratory milling, fluid energy milling, jet milling and ball milling. Ball milling is the preferred method.

The resulting fillers comprise, contain, consist essentially or consist of aggregated nano-sized particles. If desired, this can be proven by transmission electron microscopy (TEM).

If desired, the surface of the filler particles can be surface treated. The surface-treatment can be accomplished according to a process as described in U.S. Pat. No. 6,730,156 (Windisch et al.) or U.S. Pat. No. 6,730,156 (Wu et al.). The content of these references is herewith incorporated by reference.

Once dispersed in the resin, the filler remains in an aggregated stage. That is, during the dispersion step the particles do not break up into discrete (i.e. individual) and un-associated (i.e. non-aggregated) particles.

If present, the nanocluster(s) is typically present in either of the following amounts:
Lower amount: at least 5 or at least 10 or at least 15 wt. %;
Higher amount: utmost 40 or utmost 38 or utmost 35 wt. %;
Range: 5 to 40 or 10 to 38 or 15 to 35 wt. %;
wt. % with respect to the weight of the whole curable composition.

The curable composition may also comprise x-ray visible particles.

Adding x-ray visible particles to the dental composition is beneficial in that it enables the practitioner to better identify the material if placed in the mouth of a patient and distinguish between sound dental tooth structure and the artificial material. The material becomes radiopaque.

Suitable x-ray visible particles include particles of metal oxides and metal fluorides. Oxides or fluorides of heavy metals having an atomic number greater than about 28 can be preferred. The heavy metal oxide or fluoride should be chosen such that undesirable colours or shading are not imparted to the hardened resin in which it is dispersed. For example, iron and cobalt would not be favoured, as they impart dark and contrasting colours to the neutral tooth colour of the dental material. More preferably, the heavy metal oxide or fluoride is an oxide or fluoride of metals having an atomic number greater than 30. Suitable metal oxides are the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Suitable metal fluorides are e.g. yttriumtrifluoride and ytterbiumtrifluoride. Most preferably, the oxides and fluorides of heavy metals having an atomic number greater than 30, but less than 72 are optionally included in the materials of the invention. Particularly preferred radiopacifying metal oxides include lanthanum oxide, zirconium oxide, yttrium oxide, ytterbium oxide, barium oxide, strontium oxide, cerium oxide, and combinations thereof. Other suitable fillers to increase radiopacity are salts of barium and strontium especially strontium sulphate and barium sulphate.

The heavy metal oxide or metal fluoride particles may be surface treated. If present, x-ray visible particles are typically present in an amount of 0.1 to 20 or 1 to 15 or 2 to 10 wt. % with respect to the weight of the whole composition. The curable composition described in the present text comprises an initiator system. The initiator system is typically present in an amount of 0.1 to 5 or 0.2 to 4 or 0.5 to 3 wt. %. The initiator system comprises a photoinitiator and an organic dye.

The initiator system contributes to an efficient cure of the curable composition, controls light penetration and light scattering and thus may have an impact on mechanical and aesthetic properties.

In certain embodiments, the photoinitiator(s) can be characterized by at least one or more, sometimes all of the following parameters:
  showing a radiation absorption band within a range of 200 to 500 or 300 to 450 nm;
  having a slightly yellowish colour.

The photoinitiator should be able to start or initiate the curing or hardening reaction of the radiation curable component(s) being present in the curable composition.

The photoinitiator typically shows a light absorption band in a wave length range of 300 to 450 nm, preferably in the range of 350 to 420 nm. Suitable examples of photoinitiators typically contain a phosphine oxide moiety.

Examples of light curing initiator components include the class of acylphosphine oxides, as described in e.g. in U.S. Pat. No. 4,737,593 (Elrich et al.)

Such acylphosphine oxides are of the general formula:

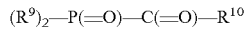

wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S—, O—, or N-containing five- or six-membered heterocyclic group, or a —Z—C(=O)—P(=O)—$(R^9)_2$ group, wherein Z represents a divalent hydrocarbyl group such as alkylene or phenylene having from 2 to 6 carbon atoms.

Preferred acylphosphine oxides are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms.

Tertiary amine reducing agents may be used in combination with an acylphosphine oxide. Illustrative tertiary amines include ethyl 4-(N,N-dimethylamino)benzoate and N,N-dimethylaminoethyl methacrylate.

Commercially-available phosphine oxide photoinitiators capable of free-radical initiation when irradiated at wavelengths of greater than 400 nm to 1,200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (previously known as IRGACURE™ 1700, Ciba Specialty Chemicals), 2-benzyl-2-(N,N-dimethylamino)-1-(4-morpholinophenyl)-1-butanone (previously known as IRGACURE™ 369, Ciba Specialty Chemicals), bis(η5-2,4-cyclopentadien-1-yl)-bis(2,6-difluoro-3-(1H-pyrrol-1-yl)phenyl) titanium (previously known as IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (previously known as DAROCUR™ 4265, Ciba Specialty Chemicals), and ethyl-2,4,6-trimethylbenzylphenyl phosphinate (LUCIRIN™ LR8893X, BASF Corp., Charlotte, NC), 2,4,6-trimethylbenzoyldiphenyl-phospine oxide (LUCIRIN™ TPO).

Exemplary UV initiators include 1-hydroxycyclohexyl benzophenone (available, for example, under the trade designation "IRGACURE 184" from Ciba Specialty Chemicals Corp., Tarrytown, NY), 4-(2-hydroxyethoxy)phenyl-(2-hydroxy-2-propyl) ketone (available, for example, under the previous trade designation "IRGACURE 2529" from Ciba Specialty Chemicals Corp.), 2-hydroxy-2-methylpropiophenone (available, for example, under the previous trade designation "DAROCURE D111" from Ciba Specialty Chemicals Corp. and bis(2,4,6-trimethylbenzoyl)-phenylposphineoxide (previously known as "IRGACURE 819" from Ciba Specialty Chemicals Corp.). The most preferred acylphosphine oxide is bis(2,4,6-trimethylbenzoyl)phenyl phosphine oxide (OMNIRAD™ 819, IGM Resin B.V., Waalwijk, NL).

The photoinitiator(s) is typically present in the following amounts:
  Lower amount: at least 0.01 or at least 0.05 or at least 0.1 wt. %;
  Upper amount: at most 3 or at most 2 or at most 1.5 wt. %;
  Range: 0.01 to 3 or 0.05 to 2 wt. % or 0.1 to 1.5 wt. %;
  wt. % with respect to the weight of the whole composition.

The polymerizable composition described in the present text also comprises one or more organic dye(s).

The nature and structure of the organic dye(s) is not particularly limited unless the desired result cannot be achieved.

It was found that by adding an organic dye, the ability of the polymerizable composition described in the present text to absorb radiation can be enhanced.

In addition, it was found that adding an organic dye contributes to supress or to lower the transmission of scattered light in the polymerizable composition. This often helps to improve the accuracy or detail resolution of the surface of the 3-dimensional article obtained from the additive manufacturing process.

In certain embodiments, the organic dye(s) can be characterized by at least one, more, of all of the following parameters:
  a) having a light absorption band within a wave length range of 350 to 420 nm;
  b) not having a light absorption band in the wave length range of 400 to 800 nm;
  c) comprising a terephthalate moiety.

The combination of parameters a) and b) is sometimes preferred.

Organic dyes which can be used include those containing a moiety selected form terephthalate groups and/or aromatic (hetero) cycles or other systems with delocalized pi-electrons. In particular dyes useful for colouring food were found to be useful.

Dye(s) which can be used include Lumilux™ Blue, Lumilux™ Yellow (Honeywell) and mixtures thereof.

If present, the organic dye(s) is present in the following amounts:
  Lower amount: at least 0.001 or at least 0.002 or at least 0.005 wt. %;
  Upper amount: at most 0.5 or at most 0.2 or at most 0.1 wt. %;
  Range: 0.001 to 0.5 or 0.002 to 0.2 or 0.005 to 0.1 wt. %; wt. % with respect to the weight of the whole composition.

The curable composition described in the present text may also comprise one or more additive(s).

Additive(s) include stabilizer(s), pigment(s), and mixtures thereof.

There is no need for additives to be present, so no additive(s) might be present at all. However, if present, they are typically present in an amount which is not detrimental to the intended purpose.

According to one embodiment, the curable composition comprises one or more stabilizer(s).

The nature and structure of the stabilizer(s) is not particularly limited, either, unless the desired result cannot be achieved.

A stabilizer may extend the shelf life of the polymerizable composition, help prevent undesired side reactions, and adjust the polymerization process of the radiation curable component(s) present in the curable composition.

Adding one or more stabilizer(s) to the polymerizable composition may further help to improving the accuracy or detail resolution of the surface of the article to be produced.

In particular it was found that adding stabilizer(s) to the polymerizable composition described in the present text may help to enhance the resolution and accuracy of the SLA process by attenuating or avoiding unwanted scattering effects.

Stabilizer(s) which can be added, include free radical scavengers such as substituted and/or unsubstituted hydroxyaromatics (e.g. butylated hydroxytoluene (Ionol), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethyl amino)-methylphenol or 2,5-di-tert-butyl hydroquinone, 2-hydroxy-4-methoxybenzophenone (UV-9), 2-hydroxy-4-n-octoxybenzophenone, phenothiazine, p-methoxyphenole (MOP), 2,2,6,6-tetramethyl-piperidine-1-oxyl radical (TEMPO) and HALS (hindered amine light stabilizers) and mixtures thereof.

If present, the stabilizer(s) is present in the following amounts:
  Lower amount: at least 0.001 or at least 0.002 or at least 0.005 wt. %;
  Upper amount: at most 0.5 or at most 0.2 or at most 0.1 wt. %;
  Range: 0.001 to 0.5 or 0.002 to 0.2 or 0.005 to 0.1 wt. %;
wt. % with respect to the weight of the curable composition.

The curable composition described in the present text may comprise pigment(s).

If the curable composition is to be used in the dental or orthodontic field, the pigment(s) should not negatively affect the aesthetics of the cured material.

Ideally, the cured composition should be tooth coloured, e.g. match with a colour of the Vita™ tooth colour guide.

Pigment(s) which might be present include titania, iron oxides and mixtures thereof, If present, the pigment(s) is present in the following amounts:
  Lower amount: at least 0.001 or at least 0.005 or at least 0.01 wt. %;
  Upper amount: at most 0.02 or at most 0.05 or at most 0.5 wt. %;
  Range: 0.001 to 0.5 or 0.005 to 0.05 wt. %;
wt. % with respect to the weight of the curable composition.

The curable composition described in the present text does not contain softener(s) in an amount above 5 wt. % or above 3 wt. % with respect to the weight of the whole composition.

During an autoclave process softeners might migrate from the cured composition. This may have a negative impact on the desired properties of the cured composition. Further, the curable composition described in the present text does typically also not contain fumed silica, the surface of which has been treated with hydrophilic and/or polymerizable silanes in an amount which may negatively affect the viscosity and/or printability. The amount of fumed silica the surface of which has been treated with polymerziable silanes is typically not more than 2 wt. % or 1.5 wt. % or 1 wt. % with respect to the weight of the whole composition.

The curable composition described in the present text can be produced by combining and mixing the components of the composition. If desired, a speed mixer can be used.

Typically, the radiation curable components are provided first and the other components are added thereto.

Due to the presence of a photoinitiator, the production process is typically carried out under save-light conditions.

During storage, the composition described in the present text is typically packaged in a suitable packaging device.

The curable composition described in the present text is typically stored in container. Suitable containers include vessels, foil bags, cartridges, etc.

The volume of the respective containers is not particularly limited, but is typically in a range of 10 to 200,000 ml or from 500 to 10,000 ml.

The curable composition described in the present text can also be provided as a kit of parts comprising the curable composition and an instruction of use.

The instruction of use typically describes under what conditions the curable composition should be used.

The invention also relates to a cured article obtainable or obtained when curing the curable composition described in the present text.

As the cured article is based on the curing of the curable composition described in the present text, the cured article has basically or essentially the same chemical composition.

The cured article has typically the following properties alone or in combination:
  flexural strength: 50 to 200 MPa or 80 to 150 MPa determined according to ISO 4049:2009 using a test bar having the dimensions 6*4*25 mm, while 6 mm is the width of the test bar;
  E-modulus 1,000 to 4,000 MPa determined according DIN EN 843-2:2007 using the flexural strength method, while calculation of the modulus is done in the range of 20% and 50% of maximum force of the samples;
  impact strength: 5 to 15 kJ/m$^2$ determined according to DIN 53453:175-05;
  abrasion: less than 20 or less than 15 or less than 10 mm$^3$ (determined as described in the example section);
  being autoclaveable without a significant change (e.g. +/−10%) of mechanical properties;
  being tooth coloured.

The combination of the following features is often preferred: high impact strength combined with low abrasion.

A sufficient flexural strength is beneficial because the material of the crown will not break easily.

A sufficient low E-modulus is beneficial because the material of the crown has a sufficient flexibility.

A sufficient impact strength is beneficial because the material of the crown has a high toughness and can resist to fracture A sufficient abrasion is beneficial because the crown will not abrade and maintain its anatomical shape during chewing. According to one embodiment, the cured article is a dental article.

Dental article can have different shapes, like the shape of a dental crown, bridge, inlay, onlay, veneer, table-top or parts thereof. A table-top refers to a crown preparation where only the upper part (i.e. the chewing surface) of the crown is prepared. A table-top is sometimes also referred to as "occlusion cap".

According to a preferred embodiment, the dental article has the shape of a preformed dental composite crown. The shape of a dental composite crown is typically characterized as follows:

The preformed crown has a top surface and depending buccal, respectively labial, mesial, distal, lingual, respectively palatinal side surfaces.

The side surfaces are connected to each other and form a crown cervix. The lower region of the crown cervix forms the crown margin or crown rim.

The preformed dental composite crown has an outer and an inner surface. The inner surface is the surface to be attached to a prepared dental tooth.

The wall thickness of the preformed crown at the crown cervix (in a distance of 1 mm from the crown margin) is equal to or lower than 0.8 or equal to or lower than 0.7 or equal to or lower than 0.6 mm or in a range of 0.1 to 0.8 mm or 0.1 to 0.7 mm or 0.1 to 0.6 mm or 0.1 to 0.5 mm.

The wall thickness of the top surface (occlusal and/or distal) of the preformed crown is typically in the range of 0.15 mm to 1.5 mm or in the range of 0.4 mm to 1.0 mm.

At least two of the opposing and depending side surfaces of the preformed dental composite crown have a concave shape, preferably the buccal and lingual side surfaces. That is, the side walls of the preformed crown have a curved shape and thus provide an undercut in the region of the crown cervix.

If desired, the dimension of the undercut U in mm can be calculated by the formula U=D2−D1, wherein D1 is the distance of the opposing inner side walls having a concave shape of the preformed crown measured 1 mm above the crown cervix, if the preformed crown is cut into halves and wherein D2 is the maximum distance of said opposing inner side walls of the crown measured parallel to D1.

In one embodiment, the shape of the preformed dental composite crown is further characterized by either of the following features alone or in combination:

The wall thickness of the side surfaces of the crown is typically not larger than 0.7 mm or 0.6 mm or 0.5 mm or 0.4 mm.

According to one embodiment, the wall thickness of the side surfaces of the preformed crown is in a range of 0.1 mm to 0.7 mm. According to another embodiment, the wall thickness of the side surfaces of the preformed crown is in a range of 0.1 mm to 0.6 mm. According to another embodiment, the wall thickness of the side surfaces of the preformed crown is in a range of 0.1 mm to 0.5 mm. According to a further embodiment, the wall thickness of the side surfaces of the preformed crown is in a range of 0.1 mm to 0.4 mm.

Such a shape is described e.g. in EP application number EP 16158959.3 (filed Mar. 7, 2016). The content of this document is herewith incorporated by reference.

The preformed dental composite crown has typically two kinds of surfaces: an outer surface being visible after fixation of the dental article in the mouth of a patient and an inner surface becoming invisible after fixation of the dental article in the mouth of a patient.

According to one embodiment, the inner surface of the preformed dental composite crown is roughened (e.g. by sandblasting) and/or has retention elements. This feature may help to enhance adhesion of the crown to the surface of a prepared dental tooth.

According to one embodiment, the outer surface of the preformed dental composite crown is polished.

During storage the cured article is typically provided in a suitable packaging device.

Suitable packaging devices include sealed blisters, plastic cases, trays or refill boxes.

The cured article described in the present text can be obtained by polymerizing the curable composition described in the present text.

The polymerizing can be done by applying an additive manufacturing technique.

Such a technique is in particular useful, if the production of individualized articles is desired.

The polymerizable composition described in the present text can be processed as construction material in an additive manufacturing process, in particular in a stereolithography process (SLA).

According to one embodiment, the additive manufacturing process comprises the steps of
 providing a layer of the construction material on a surface,
 radiation curing those parts of the layer of construction material which will belong to the 3-dim article to be produced,
 providing an additional layer of the construction material in contact with the radiation cured surface of the previous layer,
 repeating the previous steps until a 3-dim article is obtained.

Such a process comprises the step of applying radiation to the surface of a radiation curable material, wherein the radiation is applied only to those parts of the surface which will later form a part of the article to be produced.

Radiation can be applied by using e.g. a laser beam or by mask-image projection. Using a mask-image projection based stereolithographie process (MIP-SL) is sometimes preferred, as it allows a more rapid manufacturing of the article.

A MIP-SL process can be described as follows:
 i. A three-dimensional digital model of the article to be produced is provided.
 ii. The three-dimensional digital model is sliced by a set of horizontal planes.
 iii. Each thin slice is converted into a two-dimensional mask image.
 iv. The mask image is then projected with the aid of a radiation source onto the surface of the radiation curable material being located in a building platform (e.g. having the shape of a vat).
 v. The radiation curable material is only cured in those regions which are exposed.
 vi. The building platform containing the radiation curable material or the layer of cured material is moved relative to the radiation source, wherein a new layer of radiation curable material is provided being in contact with the layer of the cured material produced in the previous step.
 vii. Steps (iv) to (vi) are repeated until the desired article is formed.

Projecting the mask image on the radiation curable material can be done either top-down or bottom-up with respect to the orientation of the vat. Using the bottom-up technique can be beneficial as less radiation curable material is needed.

In this process, the radiation cured layer is formed on the bottom of the vat, which is transparent.

It was found that the polymerizable composition described in the present text is in particular useful for processing it in a mask-image projection stereolithography process using the bottom-up projection technique.

Suitable process parameters for an SLA process include:
Wavelength of radiation: 350 to 420 nm;
Curing time: 0.5 to 20 sec.;
Layer thickness: 1 to 100 μm.

After processing the curable composition to form a 3-dim article, the 3-dim article is typically removed from the device used for conducting the additive manufacturing process.

If desired, the surface of the 3-dim article is cleaned, e.g. by rinsing the 3-dim article with a solvent.

Suitable solvents include either low boiling alcohols as described in the present text (e.g. an alcohol having a boiling point below 100° C.; like methanol, ethanol, n- or iso-propanol) and mixtures thereof or high boiling solvents as described in the present text, preferably the same solvent(s) being present in the sol, e.g. diethylene glycol ethyl ether.

If desired, the 3-dim article can be post-cured by applying radiation or heat. Such a step may help to improve the stability of the 3-dim article.

If applied, the post-curing step can be characterized by at least one, or all of the following features:
applying radiation with wavelength of 350 to 450 nm;
applying a heating step of 30 to 120 or from 40 to 80° C.

Thus, a suitable process of processing the curable composition described in the present text may comprise the following steps:
a) providing the curable composition as described in the present text,
b) producing a cured article precursor with a 3d-printer having a vat by radiation curing the curable composition, the cured article having an outer and an inner surface,
c) removing the cured article precursor from the vat of the 3d-printer,
d) cleaning the cured article precursor,
e) post-curing the cured article precursor to obtain a cured article,
f) optionally removing any support structures, if present
g) optionally polishing at least parts of the outer surface of the cured article,
h) optionally sandblasting at least parts of the inner surface of the cured article.

If desired, step c) can also be accomplished after step d) or after step e).

According to one embodiment, the cured article has the shape of a preformed dental composite crown.

The cured article precursor may comprise supporting elements, which support and carry the cured article precursor during the 3d-printing process. If present, the supporting elements are removed later in the process, e.g. after step c), d) or e).

The invention also relates to a kit of parts comprising at least two cured articles described in the present text, wherein the cured articles have the shape of a dental crown.

A kit can comprise up to 200 or up to 150 differently shaped preformed dental composite crowns.

A kit can comprise each of the differently shaped preformed dental composite crowns in an amount up to 10 or up to 8 different sizes.

The preformed dental composite crowns can have the shape of an anterior or posterior tooth.

Typically, the preformed dental composite crowns are provided in different tooth colors. Tooth colors are typically classified according to the Vita' color code.

The invention also relates to a kit of parts comprising at least one cured article having the shape of a dental article obtained by radiation curing the curable composition described in the present text and one or more of the following items:
dental cement,
instruction for use.

Thus, the kit of parts can also comprise a dental cement suitable for securely fixing the preformed dental composite crown to a prepared tooth surface.

Suitable dental cements are glass ionomer cements and in particular resin modified glass ionomer cements. Glass ionomer cements typically contain the following components: acid-reactive filler, polyacid, water, and complexing agent, but no radiation curable components.

Glass ionomer cements are typically provided as a kit of part comprising a liquid part and a powder part. The two parts have to be mixed before use.

The powder part typically comprises an acid-reactive inorganic filler (e.g. a fluoro alumosilicate glass, FAS glass).

The liquid part typically comprises a polyacid, water and a complexing agent (e.g. tartaric acid).

Glass ionomer cements are commercially available (e.g. Ketac™ Cem; 3M Oral Care).

The glass ionomer cement can also be provided as a kit of parts comprising two pastes A and B to be mixed before use.

According to a preferred embodiment, the kit of parts containing the preformed dental composite crowns comprises a resin modified glass ionomer cement (RM-GIZ).

Resin modified glass ionomer cements typically contain the following components: acid-reactive filler, polyacid, water, complexing agent, radiation curable components, initiator.

Suitable radiation curable components typically contain (meth)acrylate moieties.

Resin modified glass ionomer cements are provided as kit of parts as well, either as powder/liquid system or paste/paste system.

The powder part typically comprises acid-reactive inorganic filler(s) (e.g. a fluoro alumosilicate glass, FAS glass) and initiator components.

The liquid part typically comprises polyacid, water, (meth)acrylates and initiator components.

Resin modified Glass ionomer cements are commercially available (e.g. Ketac™ Cem Plus; 3M Oral Care).

It was surprisingly found that in particular a RM-GIZ is suitable for securely fixing the preformed dental composite crown to the surface of a prepared tooth.

Even, if a little bit more expensive than classical glass ionomer cements, RM-GIZ can be obtained at a lower expense compared to self-adhesive resin cements (e.g. RelyX™ Unicem or adhesive resin cements (e.g. RelyX™ Ultimate; 3M Oral Care).

According to one embodiment, the cured article described in the present has the shape of a dental article, in particular the shape of a preformed dental composite crown.

The preformed dental composite crown described in the present text is used for treating a dental tooth, in particular in the pediatric field.

Such a method comprises the step of fixing the preformed dental composite crown as described in the present text to the surface of a prepared tooth in the mouth of a patient by using a dental cement as described in the present text, in particular a resin modified glass ionomer cement.

If desired, the surface of the preformed dental composite crown which is to be attached to the surface of the prepared tooth ("inner surface") can be roughened before the dental cement is applied. Roughening can be done e.g. sandblasting.

Roughening the surface can be useful to even further improve the fixation of the preformed crown to the prepared surface of the tooth to be treated.

If desired, the shape of the preformed dental composite crown can be further adapted by a cutting or grinding.

According to one embodiment the curable composition as described in the present text comprises:
  polymerizable (meth)acrylate(s) not comprising a urethane moiety
    comprising at least two (meth)acrylate moieties,
    having a molecular weight of 170 to 3,000 g/mol, and
    being present in an amount of 40 to 85 wt. %,
  the polymerizable urethane(meth)acrylate(s)
    comprising at least three urethane moieties,
    having a molecular weight of 450 to 3,000 g/mol, and
    being present in an amount of 1 to 35 wt. %,
  nanocluster
    comprising Si or Zr based particles, and
    being present in an amount of 5 to 40 wt. %,
  optionally fumed silica
    being present in an amount of 0.5 to 7 wt. %,
  X-ray visible particles
    being present in an amount of 0 to 15 wt. %
  photoinitiator
    comprising a phosphine oxide moiety, and
    being present in an amount of 0.01 to 3 wt. %,
  stabilizer being present in an amount of 0.001 to 0.5 wt. %,
  organic dye in an amount of 0.001 to 5 wt. %,
  the curable composition not comprising
    softener in an amount of more than 5 wt. %,
  wt. % with respect to the weight of the whole composition.

The components used for producing the curable composition and in particular the dental articles described in the present text should be sufficiently biocompatible, that is, the composition should not produce a toxic, injurious, or immunological response in living tissue.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate the invention.

Examples

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).

Methods

Viscosity

The viscosity has been measured using a Physica Rheometer MCR 301 device with a plate-plate system (diameter 15 mm) and a slit of 0.2 mm. The viscosity values (Pas) were recorded at 23° C. for a shear rate of 1 $s^{-1}$.

Flexural Strength

If desired, flexural strength can be determined by conducting a three point flexural strength test according to ISO 4049:2009 using test specimen having the size 4*6*25 mm. Flexural strength is given in [MPa].

E-Modulus

The E-Modulus was determined according to DIN EN 843-2:2007 using a test bar having the dimensions 6*4*25 mm, with 6 mm being the width of the sample. The E-Modulus was determined between the range of 20% and 50% of the maximum force of the test specimen. E-Modulus is given in [GPa].

Impact Strength

If desired, the impact strength can be determined according to DIN 53453:1975-05 (Charpy) using test samples having the dimensions 4*6*50 mm, using a Zwick 5102 pendulum set up with a 0.5 J pendulum and using a span of 42 mm. Impact strength is given in [$kJ/m^2$].

Abrasion

If desired, abrasion [$mm^3$] can be determined as follows: Abrasion tests were performed at specific specimens with a slope of 30°. For that purpose the materials were filled into the depression of M12 Inbus-screws and cured according to the manufacturers' instructions.

The specimens were flat grinded using a 75 μm diamond saw and stored in distilled water for 4 days at 36° C. Then chewing simulation was started applying the following conditions:

Chewing force: 80 N; Lateral movement: 4 mm; Sliding movement: 10 mm; Antagonist: steatite ball; Number of chewing cycles: 1,200,000; Thermocycles (5/55° C.): 5,000.

After conducting the chewing simulation abrasion was determined by measuring the loss of volume using a laser scanning microscope VK-X200 (Keyence Company).

Further information about the abrasion test can be found in M. Rosentritt et al., Materialprüfung 39 (1997), p. 77-80.

Evaluation of Printability

Two different printing setups were used, each containing at least 2 article precursors on the printing platform:
  Printing Setting 1: distance of the article precursors was 2 mm or less.
  Printing Setting 2: distance of the article precursors was at least 3 mm.

A lower distance between the article precursors allows the simultaneous printing of a higher number/volume of articles on a given printing platform and thus a more efficient manufacturing process.

After the printing process, the printed article precursors were visually evaluated and classified as "YES", if the geometrical dimensions of the printed article precursor matched with the geometrical dimensions of the respective STL file and "NO", if the geometrical dimensions of the printed article precursor did no match with the geometrical dimensions of the respective STL file.

Materials

TABLE 1

| | | |
|---|---|---|
| Zr/Si Nanocluster | aggregated nanoparticles; nanoclusters; filler | U.S. Pat. No. 6,730,156 B1, column 25, Preparatory Example A; the obtained filler particles were surface treated according to Preparatory Example B of U.S. Pat. No. 6,730,156 B1. |
| HDK ™ H-2000 | fumed silica filler; surface modification: —OSi(CH$_3$)$_3$; agglomerated nanoparticles | |
| Aerosil ™ R711 | fumed silica filler; surface modification: methacryl silane | |
| SG-YBF100 | ytterbium fluoride powder; filler | |
| D-Zethacrylate | ethoxylated Bisphenol A dimethacrylate; polymerizable methacrylate | |
| DESMA | urethane(meth)acrylate; polymerizable methacrylate | Example 1 of EP 2 167 013 B1 (page 20) |
| GDMA | Glycerol dimethacrylate | |
| Ionol ™ | 2,6-ditert.butyl-4-methylphenol; stabilizer | |
| Z-Acetate | ethoxylated Bisphenol A diacetate; softener | |
| TEGDMA | Triethylenglycole dimethacrylate | |
| Lucirin ™ TPO | Photoinitiator | |
| Ircacure ™ 819 | Photoinitiator | |
| Lumilux ™ Blau LZ | Organic dye | |

The compositions outlined in Table 2 were prepared. The amount of the components is given in parts by weight (pbw):

TABLE 2

| | Ex1 (CE) | Ex2 (CE) | Ex3 (CE) |
|---|---|---|---|
| Lucirin TPO | — | — | — |
| Ircacure 819 | — | 0.54000 | 0.54000 |
| Lumilux Blau LZ | 0.00136 | 0.00136 | 0.00136 |
| Cu-Procetonat | 0.00273 | — | — |
| Amine-HCl | 0.17273 | — | — |
| Ionol | 0.02727 | 0.02727 | 0.02727 |
| D-Zethacrylat | 39.96591 | 39.96727 | 39.96727 |
| DESMA | 4.37545 | 4.37545 | 4.37545 |
| HDK H-2000 | 4.54545 | 4.54545 | 4.54545 |
| SG-YBF 100 | 2.27273 | 2.27273 | 2.27273 |
| Aerosil R711 | 1.81818 | 1.81818 | 1.81818 |
| Zr/Si-Nanocluster | 38.63636 | 38.63636 | 38.63636 |
| TBPIN | 0.02727 | — | — |
| BZPBS | 0.90909 | — | — |
| Z-Acetate | 7.24545 | 7.24545 | — |

| | Ex4 (CE) | Ex5 (CE) | Ex6 (IE) | Ex7 (CE) |
|---|---|---|---|---|
| Lucirin TPO | — | 0.54000 | 0.54000 | 0.54000 |
| Ircacure 819 | 0.54000 | — | — | — |
| Lumilux Blau LZ | 0.00136 | 0.00136 | 0.00136 | 0.001492 |
| Cu-Procetonat | — | — | — | — |
| Amine-HCl | — | — | — | — |
| Ionol | 0.02727 | 0.02727 | 0.02727 | 0.0497 |
| D-Zethacrylat | 39.96727 | 39.96727 | 39.96727 | 0.1477 |
| GDMA | — | — | — | 29.7186 |
| DESMA | 4.37545 | 4.37545 | 4.37545 | 19.8124 |
| HDK H-2000 | 4.54545 | 4.54545 | 1.70000 | 3.9794 |
| SG-YBF 100 | 2.27273 | 2.27273 | 2.27273 | 2.4865 |
| Aerosil R711 | 1.81818 | 1.81818 | — | 0.9946 |
| Zr/Si-Nanocluster | 18.20000 | 18.20000 | 18.20000 | 42.2705 |
| TBPIN | — | — | — | — |
| BZPBS | — | — | — | — |
| Z-Acetate | — | — | — | — |

CE: Comparative Example; IE: Inventive Example

The composition of Ex1 essentially corresponds to the composition described in example 1 of WO 2015/006087 A1 and functions as a comparative example (CE).

In the composition of Ex2 the redox initiator system of Ex1 has been replaced by a photoinitiator system.

In the composition of Ex3 the softening component (Z-Acetate) has been omitted.

In the composition of Ex4 the amount of filler has been reduced.

In the composition of Ex5 the photoinitiator system has been switched.

In the composition of Ex6 the amount of methaycrylsilane treated silica has been reduced.

The composition of Ex7 essentially corresponds to the composition described in example 3 of US 2016/0136059 A1 (Hecht et al.) except that a photo initiator system was used instead of a redox curing initiator system.

General Processing of Curable Compositions

For the curable compositions Ex1 given in Table 2, the components were provided and mixed using a kneader to obtain homogenous paste A and paste B. The pastes were filled in a dual chamber cartridge with a volume of Paste A to Paste B of 10:1 (SulzerMixpac). The composition was dispensed through a static mixing tip (SulzerMixpac) by using a manually driven gear into moulds having the geometry of 4 mm×6 mm×25 mm, removed after 1 h and stored into de-ionized water for 24 h.

For the curable compositions of Ex2, Ex3, Ex4, Ex5 and Ex6, the components were provided and mixed using a kneader to obtain a homogenous paste. The paste was poured into the working tray of a commercially available DLP printer (Rapidshape HA30; Heimsheim, Germany).

The pre-processing data (STL-file; shape of 3-dim. Object; 4 mm×6 mm×25 mm) was loaded into the printer.

The following printing conditions were applied:
  curing light wavelength: 383 nm light;
  exposure time: 11 sec;
  layer thickness: 50 μm;
  printing protocol: using the standard parameter set for material GP101 (Software: Netfabb Professional for Rapidshape 5.2 64 bit).

The article precursors were finished by applying the following steps:

removing the article precursor from the building platform cleaning the article precursor for 5 min in isopropanol using ultrasonic device (Fa. BANDELIN electronic GmbH & Co. KG, DT 100 H)

light curing the article precursor for 900 sec under argon conditions.

The obtained cured articles were tested with respect to viscosity and printing properties as outlined in Table 3. A viscosity above 150 Pa*s was considered as too high for a proper processing.

TABLE 3

|  | Ex1 | Ex2 | Ex3 | Ex4 | Ex5 | Ex6 | Ex7 |
|---|---|---|---|---|---|---|---|
| Radiation curability | No | Yes | Yes | Yes | Yes | Yes | Yes |
| Printing Setting 1 | n.d. | No | No | No | No | Yes | n.d. |
| Printing Setting 2 | n.d. | n.d. | n.d. | Yes | n.d. | Yes | n.d. |
| Viscosity in [Pas] at shear rate 1 [$s^{-1}$] | n.a. | 217 | 357 | 195 | 202 | 18.2 | 268 | n.d. = not determined

Further, the obtained cured articles were tested with respect to the mechanical properties as outlined in Table 4 before and after having conducted an autoclave process simulated by applying the following conditions: placing the cured article in an oven for 24 h at 120° C.

|  |  | Ex1 | Ex4 | Ex6 |
|---|---|---|---|---|
| initial values | Elastic Modulus in Gpa | 3.1 | 3.8 | 2.7 |
| 24 h-120° C. | Elastic Modulus in Gpa | 3.9 | 3.6 | 2.8 |
| Delta in % | Elastic modulus | 20 | −6 | 4 |

Due to the absence of a photoinitiator, the composition of Ex1 is not radiation curable and cannot be processed in an SLA process.

The composition of Ex2 contained a photoinitiator and can thus be processes in an SLA process.

However, the printability of the precursor articles using the Printing Setup 1 was classified as not satisfying. The viscosity of the curable composition was too high.

The composition of Ex3 contained a photoinitiator but not a softener. Like the composition of Ex2, the printability of the precursor article was classified as not satisfying. The viscosity of the curable composition was too high.

The composition of Ex4 contained a lower amount of cluster filler was used. The composition was classified as being autoclaveable. Further, the viscosity of the curable composition could be lowered, but the printability of the precursor article using the Printing Setup 1 was still not satisfying.

The composition of Ex5 contained a different photoinitiator. The printability and viscosity of the composition did not significantly change.

In the composition of Ex6 the amount of silica filler has been reduced. The viscosity of the curable composition dropped significantly. The printability using the Printing Setup 1 was classified as satisfying. Further the cured composition was also cured as being autoclaveable.

What is claimed is:

1. A curable composition comprising:
a resin matrix comprising:
polymerizable (meth)acrylate(s) not comprising a urethane moiety present in an amount of 45 to 60 wt %, and
polymerizable urethane(meth)acrylate(s) present in an amount from 8 to 20 wt %;
a filler matrix present in an amount of 25 to 40 wt %, the filler matrix comprising:
nanocluster(s) present in an amount of 25 to 35 wt %;
an initiator system comprising:
photoinitiator(s),
wherein the curable composition is characterized by a viscosity below 150 Pa*s at 23° C. and a shear rate of 1 $s^{-1}$, and
wherein wt % is with respect to the weight of the curable composition.

2. The curable composition of claim 1, the polymerizable (meth)acrylate(s) not comprising a urethane moiety and the polymerizable urethane(meth)acrylate(s) present in a weight ratio of 5:1 to 1.5:1.

3. The curable composition of claim 1, the polymerizable (meth)acrylate(s) not comprising a urethane moiety comprising 1 or 2 polymerizable moieties.

4. The curable composition of claim 1, the polymerizable (meth)acrylates not comprising a urethane moiety characterized by a molecular weight of 170 g/mol to 3,000 g/mol.

5. The curable composition of claim 1, the polymerizable (meth)acrylate(s) not comprising a urethane moiety comprising bis[3 [4]-methacryl-oxymethyl-8 (9)-tricyclo [5.2.1.0$^{2,6}$]decylmethyl triglycolate, 2,2-bis-4 (3-methacryloxy-2-hydroxypropoxy)phenylpropane, 2,2-bis-4 (3-methacryloxypropoxy)phenylpropane, triethylene glycol dimethacrylate, glycerol dimethacrylate, an ethoxylated bisphenol A dimethacrylate, di(meth)acrylates of bishydroxymethyltricyclo-(5.2.1.0$^{2,6}$)decane, or a combination thereof.

6. The curable composition of claim 1, the polymerizable (meth)acrylate(s) not comprising a urethane moiety comprising an ethoxylated bisphenol A dimethacrylate.

7. The curable composition of claim 1, wherein the polymerizable urethane(meth)acrylates(s) is derived from a polyisocyanate having an isocyanurate structure.

8. The curable composition of claim 1, wherein the polymerizable urethane (meth)acrylates(s) is a reaction product of:
a polyisocyanate represented by a formula:

and
a monofunctional (meth)acrylate represented by a formula:

9. The curable composition of claim 1, wherein the polymerizable urethane(meth)acrylates(s) is represented by one or more of:

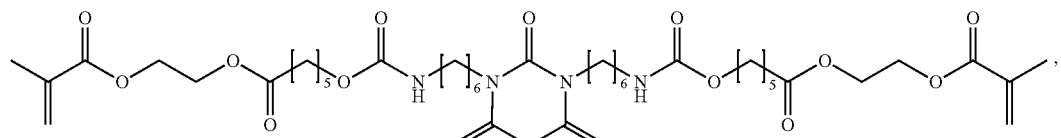

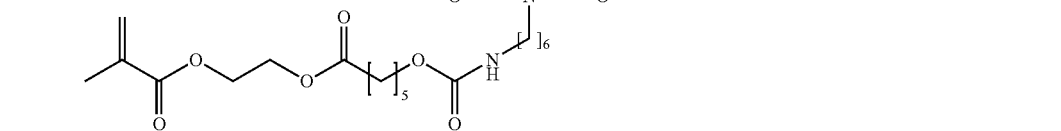

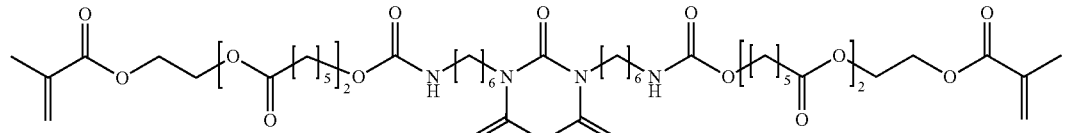

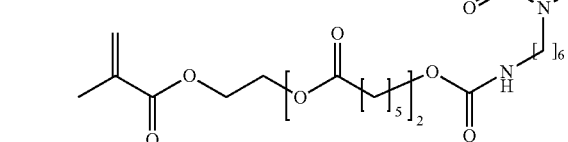

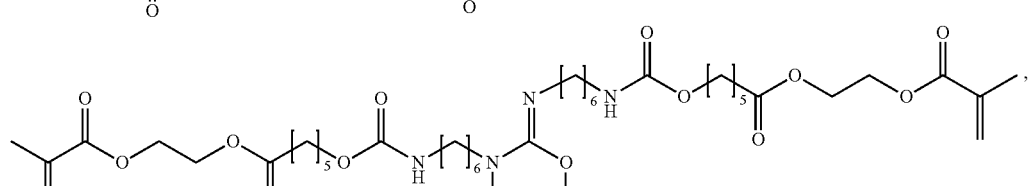

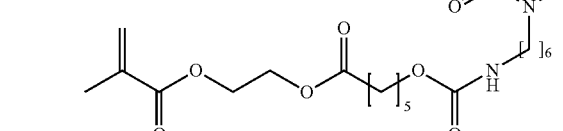

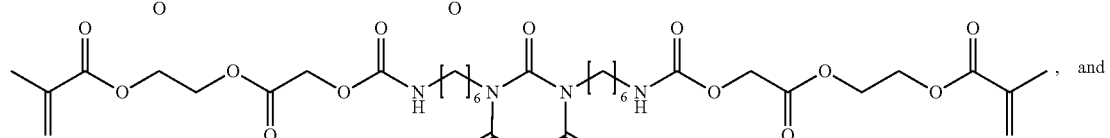

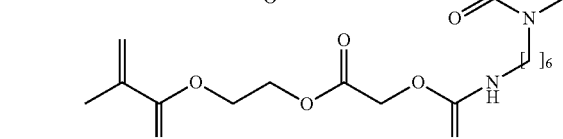

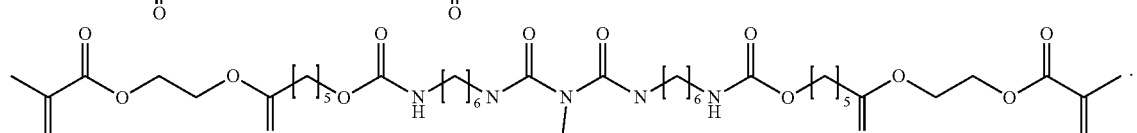

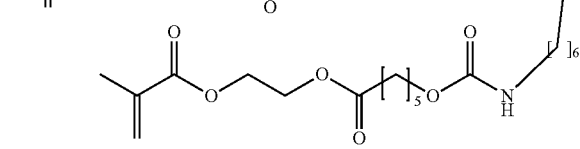

10. The curable composition of claim 1, wherein the polymerizable urethane(meth)acrylates(s) is characterized by a molecular weight of 450 g/mol to 3,000 g/mol.

11. The curable composition of claim 1, the nanocluster(s) being aggregated nanoparticles of silicon, zirconia, or a combination thereof.

12. The curable composition of claim 1, excluding a fumed silica having a surface treated with a polymerizable moieties.

13. The curable composition of claim 1, the filler matrix further comprising a fumed silica having a surface treated with a polymerizable silane, the fumed silica being present in an amount of no more than 5 wt %.

14. The curable composition of claim 1, the filler matrix further comprising a fumed silica having a surface treated with —OSi(CH$_3$)$_3$ present in an amount of no more than 5 wt %.

15. The curable composition of claim 1, further comprising organic dye(s).

16. The curable composition of claim 1, excluding a softener.

17. The curable composition of claim 1, further comprising a softener in an amount of no greater than 5 wt %.

18. The curable composition of claim 1, further comprising an ethoxylated bisphenol A diacetate as softener in an amount of no greater than 8 wt %.

19. The curable composition of claim 1, the polymerizable (meth)acrylate(s) not comprising a urethane moiety comprising an ethoxylated bisphenol A dimethacrylate, and the polymerizable urethane(meth)acrylates(s) comprising a compound of a formula:

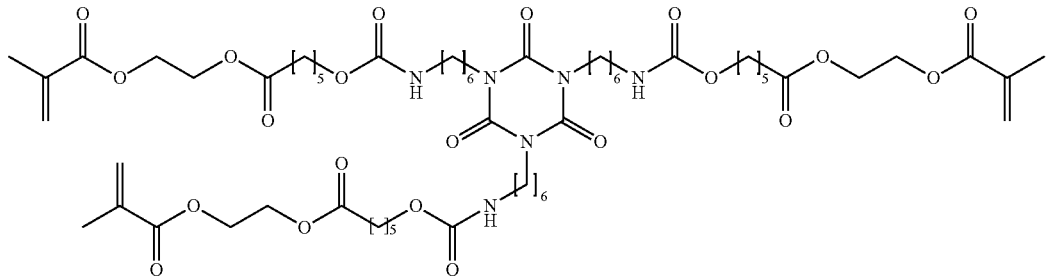

20. The curable composition of claim 1, for use is producing a dental or orthodontic article.

* * * * *